(12) United States Patent
Tamura et al.

(10) Patent No.: US 10,582,842 B2
(45) Date of Patent: Mar. 10, 2020

(54) OBSERVATION IMAGE ACQUIRING SYSTEM AND OBSERVATION IMAGE ACQUIRING METHOD

(71) Applicant: OLYMPUS CORPORATION, Tokyo (JP)

(72) Inventors: Kazuaki Tamura, Hachioji (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 442 days.

(21) Appl. No.: 15/281,709

(22) Filed: Sep. 30, 2016

(65) Prior Publication Data

US 2017/0014022 A1 Jan. 19, 2017

Related U.S. Application Data

(63) Continuation of application No. PCT/JP2015/060333, filed on Apr. 1, 2015.

(30) Foreign Application Priority Data

Apr. 2, 2014 (JP) ................................. 2014-076278

(51) Int. Cl.
*A61B 1/06* (2006.01)
*A61B 1/04* (2006.01)
(Continued)

(52) U.S. Cl.
CPC ........ *A61B 1/0638* (2013.01); *A61B 1/00009* (2013.01); *A61B 1/043* (2013.01);
(Continued)

(58) Field of Classification Search
CPC ... A61B 1/0638; A61B 1/00009; A61B 1/043; A61B 1/063; A61B 1/0653; A61B 1/07;
(Continued)

(56) References Cited

U.S. PATENT DOCUMENTS

2009/0167149 A1* 7/2009 Ito .................... A61B 1/0638
313/501
2011/0071352 A1 3/2011 Ozawa et al.
(Continued)

FOREIGN PATENT DOCUMENTS

CN 102119846 A 7/2011
JP 2009-297141 A 12/2009
(Continued)

OTHER PUBLICATIONS

International Search Report dated Jun. 23, 2015 from related International Application No. PCT/JP2015/060333.
(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A light source apparatus irradiates an observation target with first light in a wavelength region which does not include a wavelength region where an absorption peak of a target substance included in the observation target is present and second light in a wavelength region where the absorption peak is present. An image acquiring circuit includes an emphasized image information generating circuit which generates emphasized image information on the basis of first image information acquired by an imaging apparatus when the observation target is irradiated with the first light and second image information acquired by the imaging apparatus when the observation target is irradiated with the second light.

23 Claims, 8 Drawing Sheets

(51) Int. Cl.
*A61B 1/00* (2006.01)
*G02B 23/24* (2006.01)
*A61B 1/07* (2006.01)
*H04N 5/225* (2006.01)
*A61B 5/1455* (2006.01)
*A61B 5/1459* (2006.01)

(52) U.S. Cl.
CPC ............ *A61B 1/063* (2013.01); *A61B 1/0653* (2013.01); *A61B 1/07* (2013.01); *A61B 5/1459* (2013.01); *A61B 5/14556* (2013.01); *G02B 23/2469* (2013.01); *H04N 5/2256* (2013.01); *G02B 23/2484* (2013.01); *H04N 2005/2255* (2013.01)

(58) Field of Classification Search
CPC .............. A61B 5/14556; A61B 5/1459; G02B 23/2469; H04N 5/2256
See application file for complete search history.

(56) References Cited

U.S. PATENT DOCUMENTS

| | | | |
|---|---|---|---|
| 2011/0172492 A1 | 7/2011 | Erikawa | |
| 2012/0253122 A1 | 10/2012 | Minetoma et al. | |
| 2018/0228355 A1* | 8/2018 | Daidoji | A61B 1/00009 |
| 2018/0368670 A1* | 12/2018 | Watanabe | A61B 1/00009 |
| 2019/0282135 A1* | 9/2019 | Ito | A61B 1/0646 |

FOREIGN PATENT DOCUMENTS

| | | |
|---|---|---|
| JP | 2011-156339 A | 8/2011 |
| JP | 2011-200367 A | 10/2011 |
| JP | 2012-005807 A | 1/2012 |
| JP | 2012-125289 A | 7/2012 |
| JP | 2012-213612 A | 11/2012 |
| JP | 2013-034753 A | 2/2013 |
| JP | 2013-233219 A | 11/2013 |
| JP | 2013-244041 A | 12/2013 |

OTHER PUBLICATIONS

Chinese Office Action dated Aug. 8, 2018 in Chinese Patent Application No. 201580016610.3.
Chinese Office Action dated Sep. 21, 2017 in Chinese Patent Application No. 201580016610.3.
International Preliminary Report on Patentability together with the Written Opinion from related International Application No. PCT/JP2015/060333 dated Oct. 13, 2016.
Japanese Office Action dated Apr. 3, 2018 in Japanese Patent Application No. 2014-076278.
Japanese Office Action dated Aug. 8, 2017 in Japanese Patent Application No. 2014-076278.
Chinese Office Action dated Apr. 18, 2019 in Chinese Patent Application No. 201580016610.3.
Chinese Office Action dated Sep. 27, 2019 in Chinese Patent Application No. 201580016610.3.

* cited by examiner

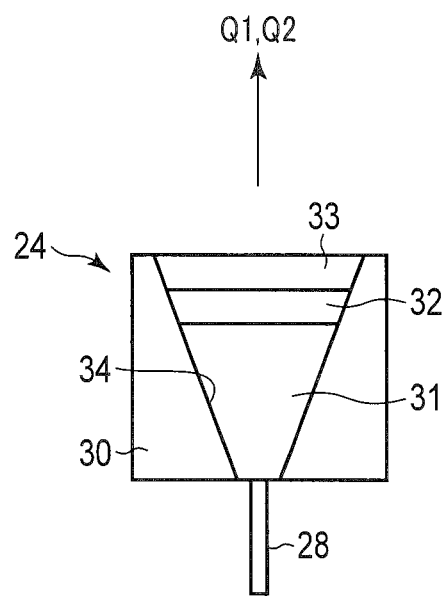
F I G. 2
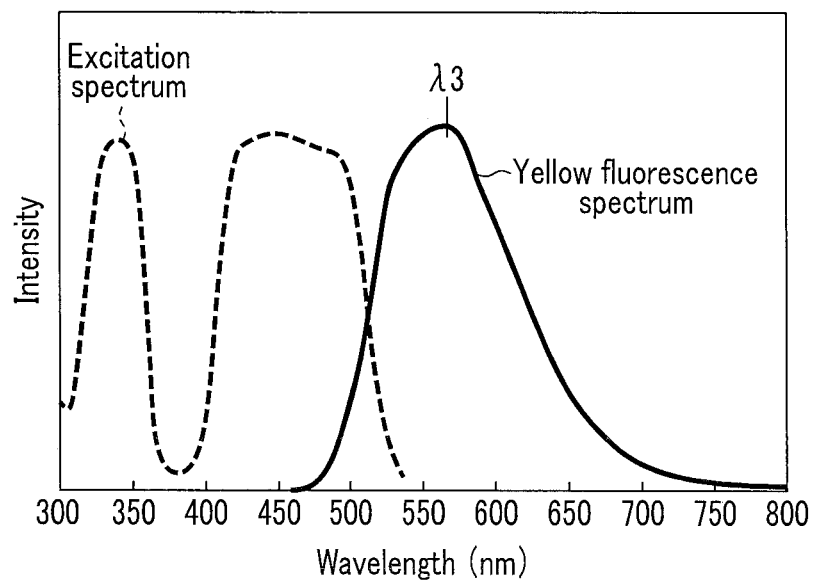
F I G. 3

OBSERVATION IMAGE ACQUIRING SYSTEM AND OBSERVATION IMAGE ACQUIRING METHOD

CROSS-REFERENCE TO RELATED APPLICATIONS

This application is a Continuation Application of PCT Application No. PCT/JP2015/060333, filed Apr. 1, 2015 and based upon and claiming the benefit of priority from the prior Japanese Patent Application No. 2014-076278, filed Apr. 2, 2014, the entire contents of which are incorporated herein by reference.

BACKGROUND OF THE INVENTION

1. Field of the Invention

The present invention relates to an observation image acquiring system and an observation image acquiring method which accomplishes, e.g., observation using white light or observation using light having a wavelength different from a wavelength of the white light, e.g., special light to observe a specific target substance.

2. Description of the Related Art

At present, there has been developed a light emitting apparatus and an endoscope apparatus using this light emitting apparatus, the light emitting apparatus outputting light from a small solid-state light source, applying this light to a wavelength conversion member arranged at an optical fiber tip to convert a wavelength, and changing the light to a desired irradiation pattern or color by this wavelength conversion.

For example, Jpn. Pat. Appln. KOKAI Publication No. 2009-297141 discloses a light source apparatus which emits white light and light in a specific narrow wavelength band (which will be referred to as special light hereinafter) on the basis of a combination of excitation light sources which have different wavelengths and wavelength converting members, and an endoscope apparatus which images each reflection light from a subject when the white light and the special light are emitted from this light source, and executes image processing to each image acquired by the imaging to generate and display a white light image and a special light image.

Further, the Publication discloses that emphasized image information by narrow band light is analytically acquired from white light image information including the narrow band lights (blue and green) and broad band light and special light image information and, for example, a blood vessel emphasized image is generated and displayed.

BRIEF SUMMARY OF THE INVENTION

According to an aspect of the present invention, there is provided an observation image acquiring system including a light source apparatus which irradiates an observation target with first light in a wavelength region which does not include a wavelength region where an absorption peak of a target substance included in the observation target is present and second light in a wavelength region where the absorption peak is present, an imaging apparatus which images the observation target to acquire image information, and an image acquiring circuit which performs an arithmetic operation for the image information acquired by the imaging apparatus to generate emphasized image information which emphasizes the target substance, wherein the image acquiring circuit comprises an emphasized image information generating circuit which generates the emphasized image information on the basis of first image information acquired by the imaging apparatus when the observation target is irradiated with the first light and second image information acquired by the imaging apparatus when the observation target is irradiated with the second light, a period that the observation target is irradiated with the second light is different to a period that the observation target is irradiated with the first light.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a specific block diagram showing a light converter in the system;

FIG. 3 is a view showing excitation/fluorescence spectral characteristics of a YAG fluorescence substance used in the light converter in the system;

DETAILED DESCRIPTION OF THE INVENTION

First Embodiment

A first embodiment according to the present invention will now be described hereinafter with reference to the drawings. In this embodiment, as regards a relationship between color regions of blue, green, and red and a visible light wavelength range, the blue color region is a region having wavelengths 380 nm to 500 nm, and the green color region is a region having wavelengths 500 nm to 600 nm, and the red color region is a region of wavelengths 600 nm to 780 nm.

Figure 1:
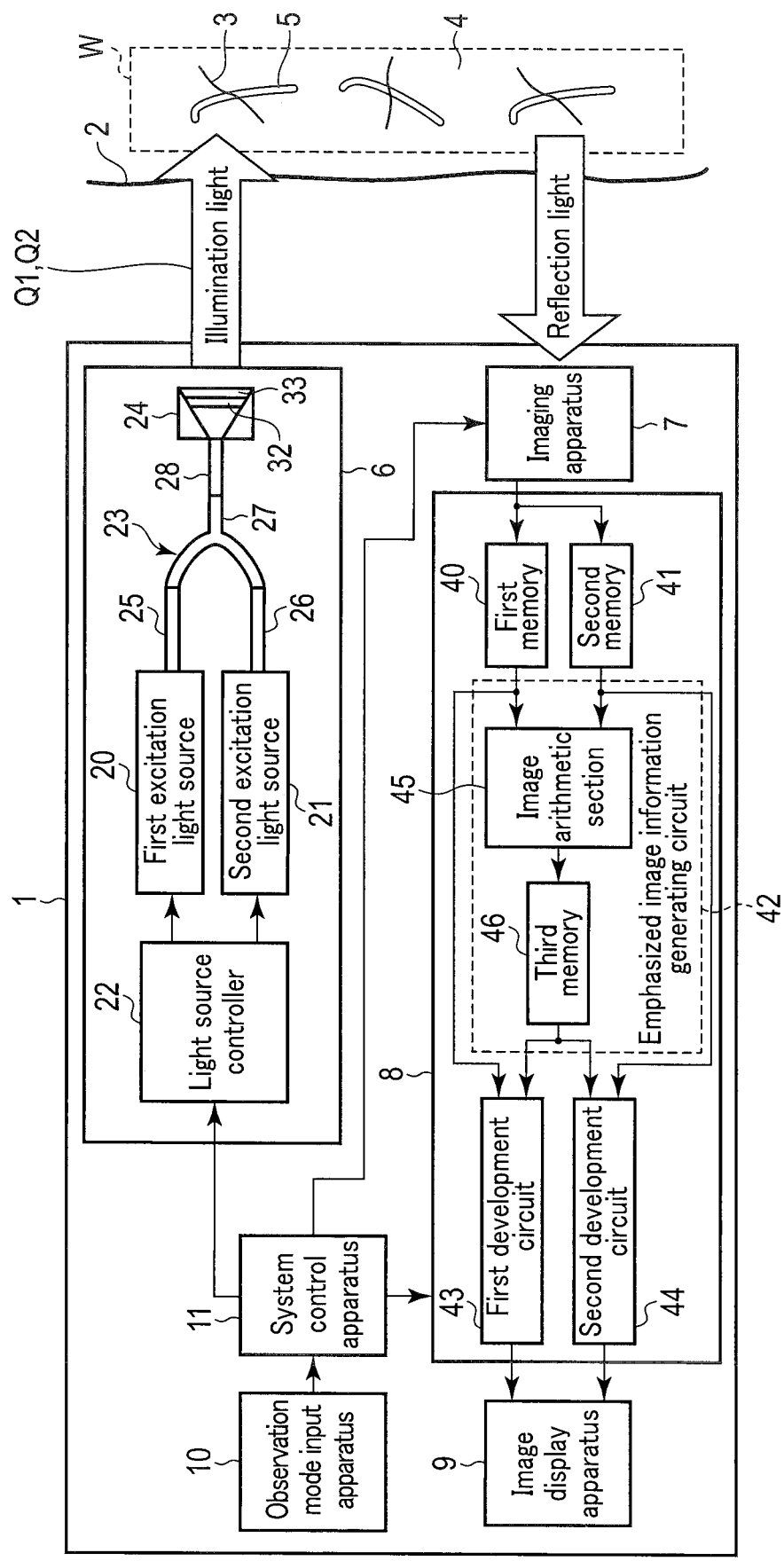
FIG. 1 is a block diagram showing a first embodiment of an observation image acquiring system according to the present invention.

FIG. 1 shows a block diagram of an observation image acquiring system 1. This system 1 generates emphasized image information to emphasize a target substance present in an observation target with increased contrast. Here, the observation target is, e.g., a subject 2 such as a human body, and includes a biotissue 4. The target substance is hemoglobin which is present in the observation target and flows through a surface layer blood vessel 3 present in a surface layer in the biotissue 4 of the subject 2 and an intermediate layer blood vessel 5 present in a deeper region than this surface layer blood vessel 3.

In this embodiment, although hemoglobin is used as the target substance, any other substance present in the body may be used, or a fluorescence probe which is administered from the outside of the body may be used. In this case, it is good to adjust an absorption wavelength region of the fluorescence probe to a wavelength of excitation light. The fluorescence probe is administered from the outside of the subject, and emits light in response to a specific wavelength.

Giving a description on a configuration of this system 1, this system 1 includes a light source apparatus 6 which irradiates the subject 2 with illumination light, an imaging apparatus (an imaging section) 7 which images reflection light from the subject 2, an image acquiring circuit 8 which generates image information of the subject 2, an image display apparatus (an image display section) 9 which displays an image of the subject 2, an observation mode input apparatus (an observation mode input section) 10 which sets an observation mode of this system 1, and a system control apparatus 11 which controls operations of the light source apparatus 6, the imaging apparatus 7, and the image acquiring circuit 8 in accordance with the observation mode set by this observation mode input apparatus 10. The image acquiring circuit 8 may be configured by a hardware circuit or a processor. If the image acquiring circuit 8 is configured by the processor, a program codes for operating the processor as the image acquiring circuit 8 when the processor executes it are stored in a processor internal memory or an external memory accessible by the processor.

The light source apparatus 6 irradiates the subject 2 with first light (first illumination light) Q1 having a peak wavelength in a wavelength region which does not include a wavelength region where an absorption peak of hemoglobin flowing through the subject 2 such as a human body is present and second light (second illumination light) Q2 having a peak wavelength in the wavelength region where the absorption peak of hemoglobin is present. This light source apparatus 6 includes a first excitation light source 20, a second excitation light source 21, a light source controller 22, a light guide 23, and a light converter 24.

The first excitation light source 20 includes a first semiconductor laser (LD) which emits a blue laser light having an emission peak wavelength of 450 nm ($\lambda 1$) and a half value width of several nm or less. In this first excitation light source 20, a blue laser light component included in the emitted blue laser light is determined as first excitation light. This first excitation light source 20 will be referred to as a first semiconductor laser 20 hereinafter.

The second excitation light source 21 includes a second semiconductor laser (LD) which emits a blue-violet laser light having an emission peak wavelength of 415 nm ($\lambda 2$) and a half value width of several nm or less. In this second excitation light source 21, a blue-violet laser light component included in the emitted laser light is determined as second excitation light. This second excitation light source 21 will be referred to as a second semiconductor laser 21 hereinafter.

The light source controller 22 controls respective drive currents supplied to the first semiconductor laser 20 and the second semiconductor laser 21, and performs control in a drive system for the first semiconductor laser 20 and the second semiconductor laser 21, e.g., pulse drive or continuous drive.

The light guide 23 guides the blue laser light emitted from the first semiconductor laser 20 and the blue-violet laser light emitted from the second semiconductor laser 21 to the light converter 24. This light guide 23 includes a first optical fiber 25, a second optical fiber 26, an optical multiplexer 27, and a third optical fiber 28.

The first optical fiber 25 is optically connected between the first semiconductor laser 20 and the optical multiplexer (a 2×1 optical coupler: two inputs-one output) 27. This first optical fiber 25 guides the blue laser light emitted from the first semiconductor laser 20 to the optical multiplexer 27.

The second optical fiber 26 is optically connected between the second semiconductor laser 21 and the optical multiplexer 27. This second optical fiber 26 guides the blue-violet laser light emitted from the second semiconductor laser 21 to the optical multiplexer 27.

The optical multiplexer 27 multiplexes the blue laser light from the first semiconductor laser 20 guided through the first optical fiber 25 and the blue-violet laser light from the second semiconductor laser 21 guided through the second optical fiber 26, and outputs a resultant light to the third optical fiber 28.

The third optical fiber 28 is optically connected between the optical multiplexer 27 and the light converter 24. This third optical fiber 28 guides the blue laser light, the blue-violet laser light, or the multiplexed light of the blue-violet laser light and the blue-violet laser light output from the optical multiplexer 27 to the light converter 24.

Thus, when the blue laser light is emitted from the first semiconductor laser 20 and the blue-violet laser light is not emitted from the second semiconductor laser 21, the optical multiplexer 27 outputs the blue laser light alone to the third optical fiber 28. Further, when the blue laser light is not emitted from the first semiconductor laser 20 and the blue-violet laser light is emitted from the second semiconductor laser 21, the optical multiplexer 27 outputs the blue-violet laser light alone to the third optical fiber 28.

Each of the first to third optical fibers 25, 26, and 28 is, e.g., a multi-mode optical fiber having a core diameter of 50 µm and a numerical aperture FNA=0.2.

Non-illustrated coupling lenses are provided between the first semiconductor laser 20 and the first optical fiber 25 and between the second semiconductor laser 21 and the second optical fiber 26, respectively. The coupling lenses converge the blue laser light emitted from the first semiconductor laser 20 or converge the blue-violet laser light emitted from the second semiconductor laser 21 to improve coupling efficiencies between the first semiconductor laser 20 and the first optical fiber 25 and between the second semiconductor laser 21 and the second optical fiber 26, respectively.

The light converter 24 is connected to an exit end side of the third optical fiber 28. This light converter 24 is excited by irradiation of the blue laser light, the blue-violet laser light, or the multiplexed light of the blue laser light and the blue-violet laser light exiting from the third optical fiber 26. This light converter 24 is excited by the blue laser light to perform wavelength conversion into white light Q1, and excited by the blue-violet laser light to perform wavelength conversion into special light Q2.

FIG. 2 shows a specific block diagram of the light converter 24. This light converter 24 includes a holder 30, a glass member 31 as a light transmitter, a first fluorescence substance 32 as a first wavelength converter, and a second fluorescence substance 33 as a second wavelength converter.

The holder 30 has a tapered holding hole 34 formed therein, and a small-diameter side of the tapered holding hole 34 functions as a laser light incidence end whilst a large-diameter side of the tapered holding hole 34 functions as an exit end from which light subjected to wavelength conversion exits. The holding hole 34 is formed so that the diameter continuously increases from the incidence end toward the exit end. The glass member 31, the first fluorescence substance 32, and the second fluorescence substance 33 are provided in this holding hole 34 from the incidence end on the small-diameter side toward the exit end on the large-diameter side.

The first fluorescence substance 32 absorbs the blue laser light having the wavelength of 450 nm ($\lambda$1) emitted from the first semiconductor laser 20, and emits fluorescence in a wavelength region showing a yellow color (which will be referred to as yellow fluorescence hereinafter). This first fluorescence substance 32 is made of, e.g., a YAG:Ce fluorescence substance (which will be referred to as a YAG fluorescence substance hereinafter).

FIG. 3 shows excitation/fluorescence spectral characteristics of the YAG fluorescence substance. When this YAG fluorescence substance is excited by the blue laser light close to the wavelength of 450 nm ($\lambda$1) in a visible light region, it emits the yellow fluorescence having high emission intensity. This yellow fluorescence spectrum has a broad spectrum whose a peak is present at a wavelength of 575 m ($\lambda$3) and whose half value with is 130 nm.

The second fluorescence substance 33 absorbs the blue-violet laser light having the wavelength of 415 nm, and emits fluorescence in a wavelength region showing a green color (which will be referred to as green fluorescence hereinafter). This second fluorescence substance 33 is made of an Eu (europium) activated sialon-based fluorescence substance (which will be referred to as a sialon fluorescence substance hereinafter).

Figure 4:
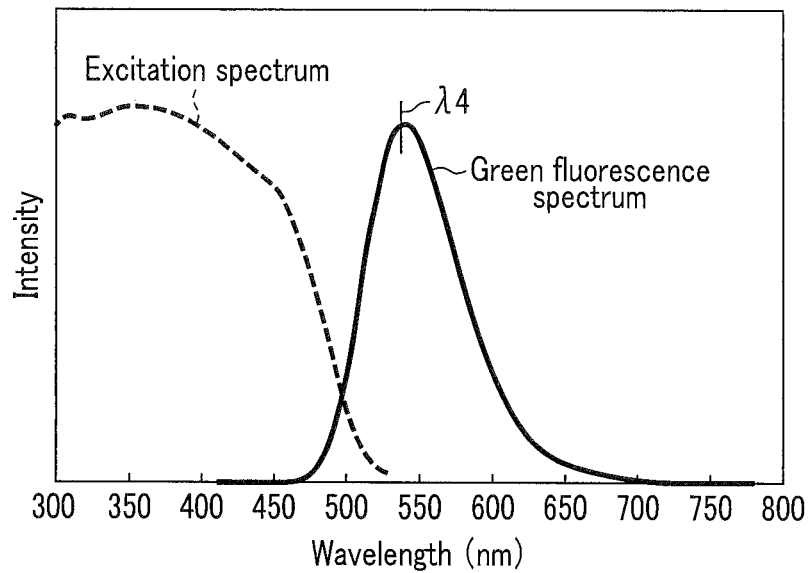
FIG. 4 is a view showing excitation/fluorescence spectral characteristics of a sialon fluorescence substance used in the light converter in the system.

FIG. 4 shows excitation/fluorescence spectral characteristics of the sialon fluorescence substance. This second fluorescence substance 33 emits the green fluorescence having higher emission intensity approaching the near-ultraviolet wavelength region. This green florescence spectrum has a broad spectrum whose peak is present at a wavelength of 540 nm ($\lambda$4) and whose half value width is 95 nm.

Each of the first and second fluorescence substances 32 and 33 is formed by dispersing a powdered fluorescence material in a sealing material such as a silicone resin or glass and solidifying the sealing material. Thicknesses of the first and second fluorescence substances 32 and 33 and a concentration of the powder fluorescence substance mixed in the sealing material are set to predetermined conditions considering characteristics such as an excitation light absorptivity of the fluorescence material or wavelength conversion efficiency. That is, the thicknesses of the first and second fluorescence substances 32 and 33 and the concentration of the powder fluorescence substance are set to predetermined conditions to convert the blue laser light into the white light Q1 provided by mixing colors of the blue laser light and the yellow fluorescence and also convert the blue-violet laser light into the special light Q2 provided by mixing colors of the blue-violet laser light and the green fluorescence.

The white light Q1 contains spectral components in the blue region, the green region, and the red region.

The special light Q2 contains spectral components in the blue region and the green region. The special light Q2 is configured to emphasize in display of a target substance such as hemoglobin in a display image. A peak wavelength of this special light Q2 is present in a wavelength region closer to an absorption peak of the target substance such as hemoglobin than a peak wavelength of the white light Q1.

Assuming that a wavelength region which corresponds to a wavelength region where the absorption peak of the target substance such as hemoglobin is present and has maximum light receiving sensitivity in respective wavelength regions of the imaging apparatus 7 is a specific color region, an emission spectral component of the special light Q2 in the specific color region has an intensity which is equal to or above that of an emission spectral component of the white light Q1.

The glass member 31 is made of glass having a high transmittance as a light transmitter and a silicone resin. This glass member 31 transmits the blue laser light, the blue-violet laser light, or the mixed light of the blue laser light and the blue-violet laser light exiting from the exit end of the optical fiber 28, the yellow fluorescence radiated from the first fluorescence substance 32, and the green fluorescence radiated from the second fluorescence substance 33.

A reflector is formed on an inner peripheral surface of the holding hole 34. This reflector regularly reflects or diffusely reflects excitation light of the blue laser light or the blue-violet laser light, yellow fluorescence emitted by the first fluorescence substance 32, and green fluorescence emitted by the second fluorescence substance 33.

Figure 5:
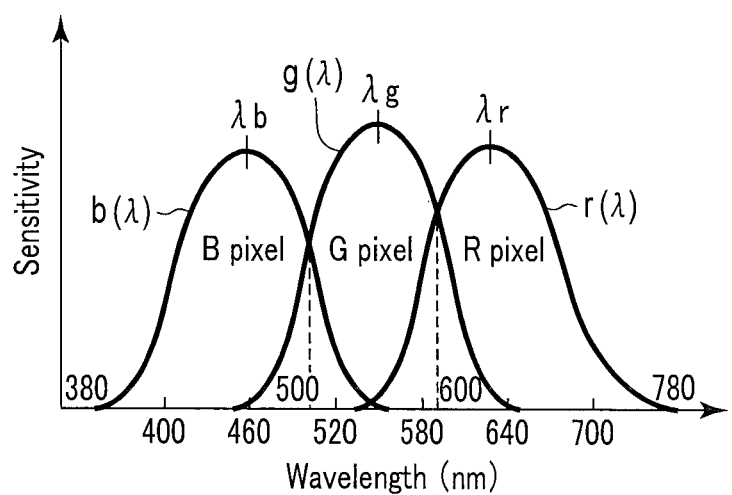
FIG. 5 is a view showing spectral sensitivity characteristics of an imaging element constituting an imaging apparatus in the system.

The imaging apparatus 7 images the subject 2, which is an observation target as described above, to acquire image information. This imaging apparatus 7 is formed by arranging imaging elements (CCDs) in longitudinal and transverse directions. These imaging elements are assigned to respective pixels of the blue (B) region, the green (G) region, and the red (R) region. That is, like the spectral sensitivity characteristics of the imaging element shown in FIG. 5, the imaging apparatus 7 includes B pixels having a sensitivity peak at a wavelength of 460 nm ($\lambda$b) in the B color region, G pixels having a sensitivity peak at a wavelength of 540 nm ($\lambda$g) in the G color region, and R pixels having a sensitivity peak at a wavelength of 630 nm ($\lambda$r) in the R color region.

When the observation target, e.g., the subject 2 is irradiated with the white light Q1, this imaging apparatus 7 acquires white light image information (B1, G1, R1) as first image information in accordance with each of pixel regions, i.e., the B color region, the G color region, and the R color region.

When the subject 2 is irradiated with the special light Q2, this imaging apparatus 7 acquires special light image information (B2, G2, R2) as second image information in accordance with each of the pixel regions, i.e., the B color region, the G color region, and the R color region.

An intensity ratio of the white color Q1 and the special light Q2 will now be described.

The white light Q1 is mixed light of the blue laser light and the yellow fluorescence emitted from the first fluorescence substance 32.

The special light Q2 is mixed light of the blue-violet laser light and the green fluorescence emitted from the second fluorescence substance 33.

The white light Q1 and the special light Q2 have different emission spectral bandwidths in the specific color region which corresponds to the wavelength region where the absorption peak of the target substance such as hemoglobin is present and which is the wavelength region having the maximum light receiving sensitivity in the respective wavelength regions of the imaging apparatus 7 as described above.

The emission spectrums of the white light Q1 and the special light Q2 do not overlap in the specific color region.

As absorption characteristics of blood vessels in the subject 2, an absorption amount of the blue-violet laser light is larger than an absorption amount of the blue laser light.

On the other hand, as sensitivity characteristics of each CCD of the imaging apparatus 7, sensitivity to the blue laser light is higher than sensitivity to the blue-violet laser light. Due to the sensitivity characteristics, to acquire blue images having substantially the same S/N with the use of the white light Q1 and the special light Q2, the blue-violet laser light in at least the B color region requires spectral intensity higher than that of the blue laser light.

Furthermore, to acquire the blue images having substantially the same S/N with the use of the white light Q1 and the special light Q2, it is preferable to switch the white light Q1 and the special light Q2 and apply them. That is, an integral of a product of an illumination light spectrum $P(\lambda)$ of the white light Q1 and sensitivity characteristics $b(\lambda)$ of the B pixels of the imaging element is determined as a first blue level B1. An integral of a product of an illumination light spectrum $Q(\lambda)$ of the special light Q2 and the sensitivity characteristics $b(\lambda)$ of the B pixels of the imaging element is determined as a second blue level B2.

The first blue level B1 and the second blue level B2 are shown as follows:

$$B1 = \int_{380}^{780} P(\lambda) \cdot b(\lambda) d\lambda$$

$$B2 = \int_{380}^{780} Q(\lambda) \cdot b(\lambda) d\lambda \qquad (1)$$

Thus, to acquire the blue images having substantially the same S/N with the use of the white light Q1 and the special light Q2, it is preferable to obtain a ratio of the blue laser light and the blue-violet laser light so that the first blue level B1 and the second blue level B2 become substantially equal to each other, switch the white light Q1 and the special light Q2 so that this ratio is provided, and irradiate the subject 2 with the switched light.

Likewise, a product of an illumination spectrum $P(\lambda)$ of the white light Q1 and sensitivity characteristics $g(\lambda)$ of the G pixels of the imaging element is determined as a first green level G1. A product of the illumination spectrum $P(\lambda)$ of the white light Q1 and sensitivity characteristics $r(\lambda)$ of the R pixels of the imaging element is determined as a first red level R1.

A product of the illumination spectrum $Q(\lambda)$ of the special light Q2 and the sensitivity characteristics $g(\lambda)$ of the G pixels of the imaging element is determined as a second green level G2. A product of the illumination spectrum $Q(\lambda)$ of the special light Q2 and the sensitivity characteristics $r(\lambda)$ of the R pixels of the imaging element is determined as a second red level R2.

The image acquiring circuit 8 performs a calculation to the image information acquired by imaging of the imaging apparatus 7, and generates emphasized image information in which the target substance, e.g., hemoglobin is emphasized with increased contrast. This image acquiring circuit 8 includes a first memory 40, a second memory 41, an emphasized image information generating circuit 42, a first development circuit 43, and a second development circuit 44. Of these members, the emphasized image information generating circuit 42 includes an image arithmetic section (an image arithmetic circuit) 45 and a third memory 46. The emphasized image information generating circuit 42, the first development circuit 43, or the second development circuit 44 may be configured by a hardware circuit or a processor. If the emphasized image information generating circuit 42, the first development circuit 43, or the second development circuit 44 is configured by the processor, a program codes for operating the processor as the emphasized image information generating circuit 42, the first development circuit 43, or the second development circuit 44 when the processor executes it are stored in a processor internal memory or an external memory accessible by the processor.

The first memory 40 temporarily stores the white light image information (B1, G1, R1) as the first image information acquired by imaging of the imaging apparatus 7 when the first semiconductor laser 20 is driven to irradiate the subject 2 with the white light Q1. This white light image information (B1, G1, R1) represents image information acquired by the B color region, the G color region, and the R color region of the imaging apparatus 7 when the subject 2 is irradiated with the white light as the first light.

The second memory 41 temporarily stores the special light image information (B2, G2, R2) as the second image information acquired by imaging of the imaging apparatus 7 when the second semiconductor laser 21 is driven to irradiate the subject 2 with the special light Q2. This special light image information (B2, G2, R2) represents image information acquired by the B color region, the G color region, and the R color region of the imaging apparatus 7 when the subject 2 is irradiated with the special light as the second light.

The emphasized image information generating circuit 42 generates the emphasized image information (B3) to emphasize, e.g., the surface layer blood vessel 3, in which hemoglobin as the target substance is present, with high contrast on the basis of the white light image information (B1, G1, R1) stored in the first memory 40 and the special light image information (B2, G2, R2) stored in the second memory 41.

Specifically, the emphasized image information generating circuit 42 includes the image arithmetic section 45 and the third memory 46, and the image arithmetic section 45 selects first color image information (B1) and second color image information (B2) of the same wavelength region, e.g., the B color region included in each of the white light image information (B1, G1, R1) and the special light image information (B2, G2, R2) as reference image information for emphasized image information generation. The image arithmetic section 45 executes a predetermined arithmetic operation for the selected first color image information (B1) and second color image information (B2) to generate the emphasized image information (B3) to emphasize, e.g., the surface layer blood vessel 3 in which hemoglobin is present with high contrast.

This image arithmetic section 45 stores the generated emphasized image information (B3) in the third memory 46. This emphasized image information (B3) has higher contrast of the surface layer blood vessel 3 than that of the white light image information (B1, G1, R1) and the special light image information (B2, G2, R2). An instruction to select the first color image information (B1) or the second color image information (B2) of the B color region is issued from the system control apparatus 11 to the emphasized image information generating circuit 42.

Two techniques will now be described as specific examples of generation of the emphasized image information (B3).

As a first technique, the image arithmetic section 45 extracts absorption difference information showing a difference in absorption of hemoglobin which is the target substance from the white light image information (B1, G1, R1) and the special light image information (B2, G2, R2), and adds this absorption difference information to the special light image information (B2, G2, R2) with strong absorption of hemoglobin to generate the emphasized image information (B3).

Specifically, the image arithmetic section 45 extracts difference information by performing an arithmetic operation to obtain a difference between the first color image information (B1) and the second color image information (B2) in the same wavelength region, e.g., B color region, and extracts the absorption difference information which is equal to or above a threshold value from the difference information. The image arithmetic section 45 generates the emphasized image information (B3) by performing an arithmetic operation to obtain a difference between the extracted absorption difference information and any one (B1 or B2) of the first color image information (B1) and the second color image information (B2) of the B color region.

As a second technique, the image arithmetic section 45 executes image noise reduction processing to image information except hemoglobin from the white light image information (B1, G1, R1) and the special light image information (B2, G2, R2), and generates the emphasized image information from the image information subjected to the image noise reduction processing.

Specifically, the image arithmetic section 45 extracts luminance information equal to or above a threshold value from luminance information of the same wavelength region, e.g., the B color region included in the special light image information (B2, G2, R2). The image arithmetic section 45 obtains luminance information by executing an arithmetic operation to obtain a difference between the extracted luminance information and luminance information of the same wavelength region, e.g., the B color region included in the white light image information (B1, G1, R1). The image arithmetic section 45 generates the emphasized image information (B3) by performing an arithmetic operation to obtain a difference between the obtained luminance information and the luminance information of the B region included in the special light image information (B2, G2, R2).

The first development circuit 43 generates emphasized image information (B3, G1, R1) of the white light by performing predetermined image processing for image information (G1, R1) which is a part of the white light image information (B1, G1, R1) stored in the first memory 40 and the emphasized image information (B3) stored in the third memory 46, and outputs a white color video signal of this white light emphasized image information (B3, G1, R1).

This first development circuit 43 generates a white light normal observation image from the white light image information (B1, G1, R1), and outputs a white color video signal of this white light normal observation image (B1, G1, R1).

Here, in the white light emphasized image information, (here, B3, G1, R1), solely hemoglobin flowing through the surface layer blood vessel 3 present in a surface layer portion in the biotissue 4 of the target substance, e.g., the subject 2 and the intermediate layer blood vessel 5 present at a deeper region than this surface layer blood vessel 3 can be emphasized while a hue of the observation target keeps conditions for a white light image. In this white light emphasized image, the target substance can be emphasized without losing white light image information of a non-target substance, e.g., a mucous membrane.

The second development circuit 44 generates emphasized image information (B3, G2) of the special light by performing predetermined image processing for image information (G2) which is a part of the special light image information (B2, G2, R2) stored in the second memory 41 and the emphasized image information (B3) stored in the third memory 46, and outputs a special color video signal of this special light emphasized image information (B3, G2). This second development circuit 44 may generate special light emphasized image information (B3, R2) by executing predetermined image processing to image information (R2) which is a part of the special light image information (B2, G2, R2) stored in the second memory 41 and the emphasized image information (B3) stored in the third memory 46, and may output a special color video signal of this special light emphasized image information (B3, R2).

This second development circuit 44 generates special light normal observation image information (B2, G2) from image information which is a part of the special light image information (B2, G2, R2), and outputs a special color video signal of this special light normal observation image (B2, G2).

The special light image information of the special light emphasized image information (B3, R2) and the special light normal observation image information (B2, G2) is generated by irradiating the subject 2 with the special light Q2 of the blue region and the green region alone. This special light image information enables observing the surface layer blood vessel 3, the intermediate layer blood vessel 5 present at a deeper region than this surface layer blood vessel 3, and others with good contrast by using a depth of the special light Q2 which enters the inside from the surface of the biotissue 4 and the fact that light scattering characteristics of this special light Q2 have different properties as will be described later, thus facilitating discovery of cancer and the like.

The first and second development circuits 43 and 44 store in a non-illustrated storage a white balance coefficient, a color conversion coefficient, and others which determine respective pieces of color information of the white light emphasized observation image (B3, G1, R1), the white light normal observation image (B1, G2, R1), the special light emphasized observation image (B3, R2), and the special light normal observation image (B2, G2). These first and second development circuits 43 and 44 perform other image processing, e.g., noise reduction, structure emphasis, color conversion, and others required for image generation by using the white balance coefficient, the color conversion coefficient, and others.

Moreover, the first and second development circuits 43 and 44 store in the non-illustrated storage an observation mode color adjustment parameter to uniformize hues of the white light emphasized observation image (B3, G1, R1) and the white light normal observation image (B1, G1, R1) and hues of the special light emphasized observation image (B3, R2) and the special light normal observation image (B2, G2). These first and second development circuits 43 and 44 apply the observation mode color adjustment parameter to various kinds of image processing by using the observation mode color adjustment parameter.

An image display apparatus 9 includes a CRT or LCD display, or the like. The image display apparatus 9 receives a video signal of the white light emphasized observation image (B3, G1, R1) or the white light normal observation image (B1, G1, R1) output from the first development circuit 43, and displays an image of this signal in the display.

The image display apparatus 9 receives a video signal of the special light emphasized observation image (B3, R2) or the special light normal observation image (B2, G2) output from the second development circuit 44, and displays an image of this signal in the display.

Figure 6:
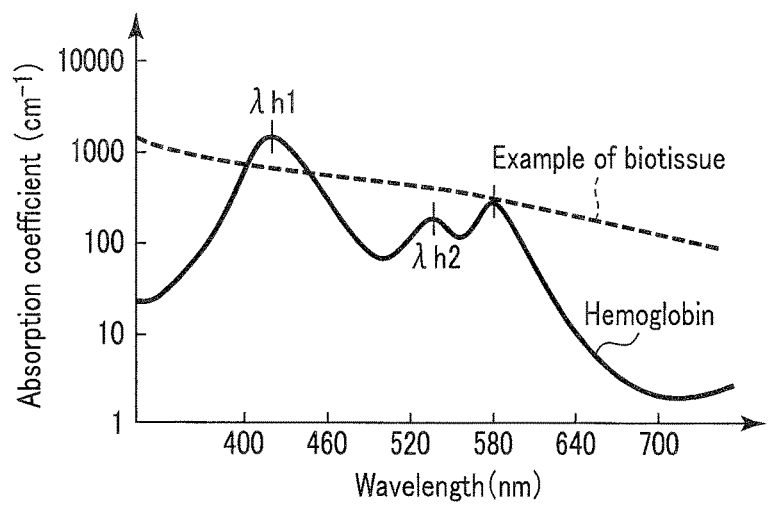
FIG. 6 is a view showing an absorption coefficient as an index of absorption intensity of hemoglobin in a blood vessel as a subject in the system.

Absorption characteristics of the subject 2 will now be described with reference to the absorption coefficient which provides an index of the absorption intensity of hemoglobin in the blood vessel shown in FIG. 6.

In the subject 2 of a human body, there are roughly two types of tissues having at least different absorption characteristics, which are the blood vessels 3 and 5, e.g., the surface layer blood vessel 3 and the intermediate layer blood vessel 5 and the biotissue 4 such as a mucous membrane. As shown in FIG. 6, the absorption intensity of hemoglobin in the blood vessels 3 and 5 have absorption intensity peaks at different wavelengths, i.e., a wavelength of approximately 415 nm ($\lambda h1$) and a wavelength of approximately 540 nm ($\lambda h2$) in the visible light region of a wavelength band of 380 nm to 780 nm. This absorption intensity of hemoglobin has properties that the absorption intensity near the wavelength of 415 nm ($\lambda h1$) becomes maximum.

In general, NBI (narrow band imaging) of an endoscope uses, as observation lights, lights having two wavelengths including the wavelength regions of the wavelength $\lambda h1$ and the wavelength $\lambda h2$, e.g., light having a wavelength of approximately 400 nm to 440 nm and light having a wavelength of approximately 525 nm to 555 nm. Additionally, NBI is a technology of observing the blood vessels 3 and 5 or the like with high contrast and facilitating discovery of cancer and the like (special light observation) due to the fact that the lights with the different wavelengths have properties that their optical penetration depths from the surface of the biotissue 4 and their scattering characteristics are different from each other.

On the other hand, the absorption characteristic of hemoglobin shows a tendency in which the absorption intensity drastically drops as the wavelength $\lambda h1$ shifts to a long wavelength. For example, when the absorption coefficient at the wavelength of 450 nm is compared with that at the wavelength of 415 nm ($\lambda h1$), a wavelength difference 35 nm between the wavelength 450 nm and the wavelength 415 nm lowers the absorption intensity of hemoglobin to approximately ⅕.

On the other hand, it is often the case that the biotissue 4 in the subject 2 of a human body or the like exhibits a flesh color to a red color. As absorption characteristics of this biotissue 4, for example, there is also a tissue whose absorption coefficient moderately lowers from the blue region to the red region, and becomes smaller than the absorption coefficient of hemoglobin near the wavelength of 415 nm and larger than the absorption coefficient of hemoglobin near the wavelength of 450 nm in the blue region.

The system control apparatus 11 is formed of a computer including a CPU, a RAM, a ROM, and others. The system control apparatus 11 issues operation commands to the light source apparatus 6, the imaging apparatus 7, and the image acquiring circuit 8 to generate/display a white light emphasized observation image (B3, G1, R1) and a special light emphasized observation image (B3, R2) by executing an observation image generation and display program stored in the ROM or the like.

Figure 7:
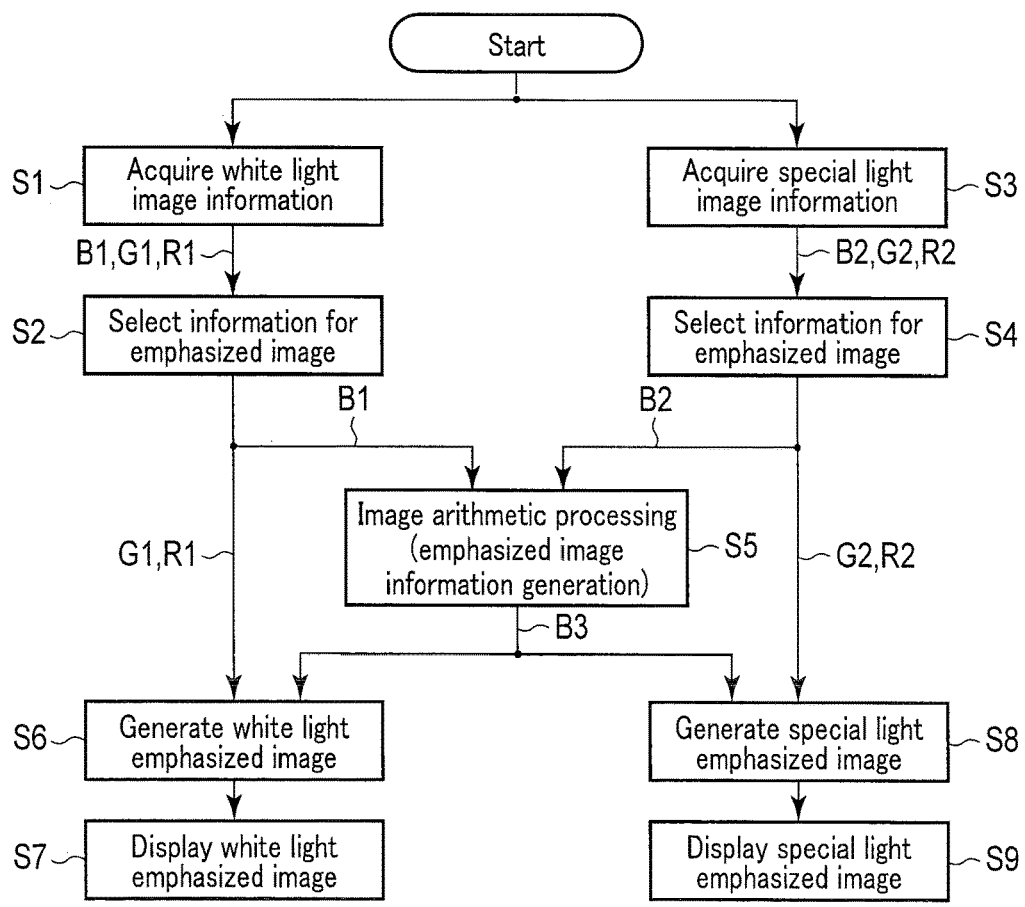
FIG. 7 is a flowchart of observation image generation and display in the system.

A description will now be given as to an operation of generating/displaying the white light emphasized observation image (B3, G1, R1) and the special light emphasized observation image (B3, G2) executed by the thus configured system 1 with reference to an observation image generation and display flowchart as shown in FIG. 7.

The observation mode input apparatus 10 sets an observation mode of this system 1 and sets an order of the observation mode upon receiving an operation of a user. It is assumed that this observation mode input apparatus 10 first sets a mode of generating/displaying the white light emphasized observation image (B3, G1, R1) and then sets a mode of generating/displaying the special light emphasized observation image (B3, G2) by an operation of the user. The observation mode input apparatus 10 may also set to generate/display the special light emphasized observation image (B3, G2) and then generate/display the white light emphasized observation image (B3, G1, R1).

Figure 8:
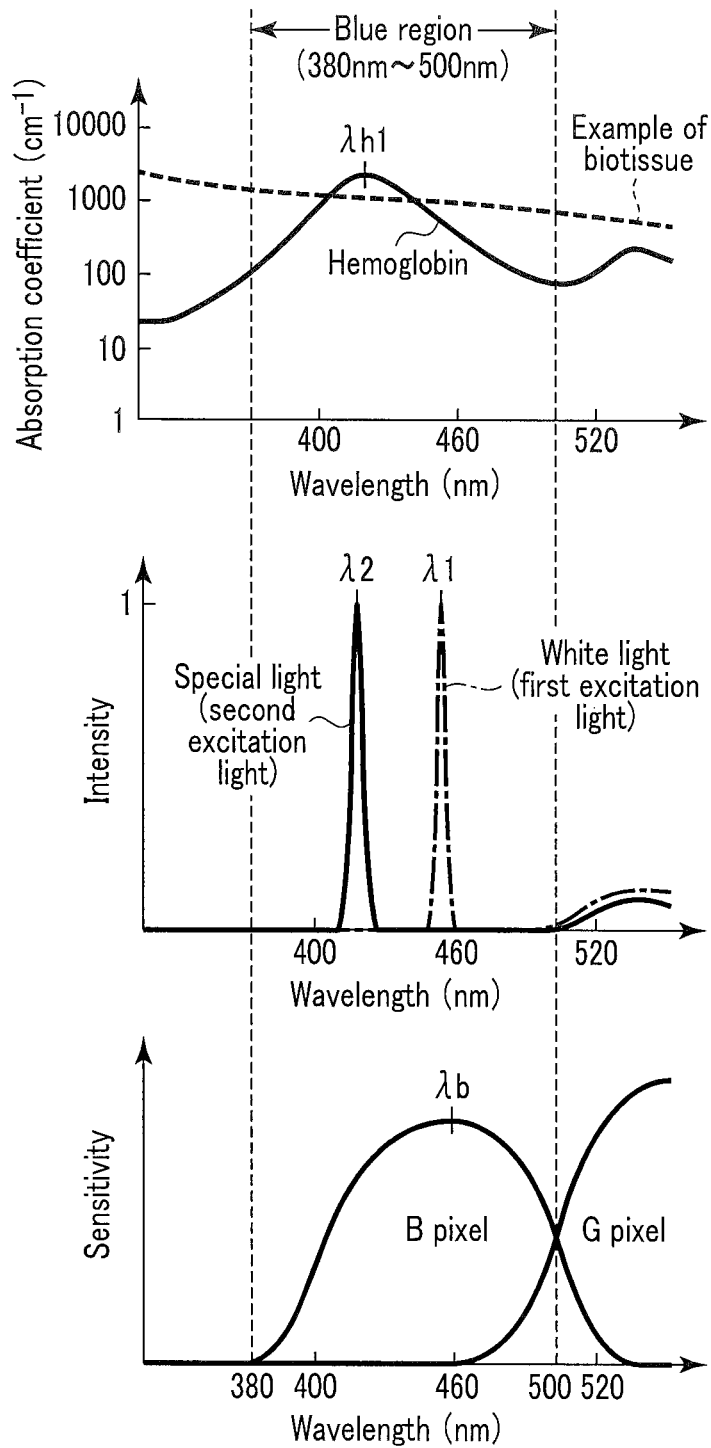
FIG. 8 is a view showing absorption characteristics of a biotissue, intensity of excitation light, and light receiving sensitivity characteristics of each color pixel in the imaging apparatus in the system.

At a step S1, the system control apparatus 11 issues to the light source controller 22 an instruction to drive the first semiconductor laser 20. This first semiconductor laser 20 emits a blue laser light having an emission peak wavelength of 450 nm ($\lambda 1$) and a half value width of several nm or less as shown in FIG. 8. When this blue laser light enters the first optical fiber 25 of the light guide 23, it is guided through the optical multiplexer 27 and the third optical fiber 28 from this first optical fiber 25 and applied to the light converter 24 as first excitation light.

When the first fluorescence substance 32 of this light converter 24 is irradiated with the blue laser light, it is excited upon absorption of this blue laser light and emits yellow fluorescence. This yellow fluorescence spectrum has a broad spectrum whose peak is present at a wavelength of 575 nm ($\lambda 2$) and whose half value width is 130 nm. Further, a part of the blue laser light is transmitted through the first fluorescence substance 32 without contributing to the yellow fluorescence. Consequently, the white light Q1 in which the yellow fluorescence is mixed with a part of the blue laser light is emitted from the first fluorescence substance 32, and the subject 2 is irradiated with this white light Q1.

When the subject 2 is irradiated with this white light Q1, this light is applied to the surface layer blood vessel 3 which is present in the biotissue 4 within an irradiation region W of the white light Q1 in this subject 2. A part of this white light Q1 is absorbed in accordance with the absorption characteristics of the surface layer blood vessel 3 through which hemoglobin flows and the biotissue 4, e.g., a mucous membrane as shown in FIG. 8, and a remaining part of the same is scattered and reflected. In this light, reflection light from the surface layer blood vessel 3 and the biotissue 4 enters the imaging apparatus 7.

The reflection light from the surface layer blood vessel 3 and the biotissue 4 enters this imaging apparatus 7, and the imaging apparatus 7 receives this reflection light by the B color region, the G color region, and the R color region of the CCDs and outputs three pieces of image information of BGR, i.e., the white light image information (B1, G1, R1). This white light image information (B1, G1, R1) is supplied to the image acquiring circuit 8, and stored in the first memory 40 of this circuit 8. The white light image information (B1, G1, R1) is stored in the first memory as three pieces of image information (B1), (G1), and (R1).

Light receiving sensitivity characteristics of the B color pixels in the imaging apparatus 7 are present in a wavelength region of 380 nm to 540 nm as shown in FIG. 8. Consequently, the reflection light from the surface layer blood vessel 3 and the biotissue 4 which is received by the B color pixels serves as a short wavelength region of the blue laser light and the yellow fluorescence. However, since the B color pixels have low sensitivity in the vicinity of a wavelength of 520 nm, a component received by the B color pixels is mainly the blue laser light.

Then, at a step S2, the system control apparatus 11 informs color information to generate the emphasized image information (B3) to the emphasized image information generating circuit 42. For example, the first color image information (B1) and the second color image information (B2) of the same wavelength region, e.g., the B color region included in the white light image information (B1, G1, R1) and the special light image information (B2, G2, R2) are informed as reference image information for emphasized image information generation.

The image arithmetic section 45 of this emphasized image information generating circuit 42 selects, e.g., the first color image information (B1) of the B color region from the white light image information (B1, G1, R1) stored in the first memory 40.

This image arithmetic section 45 selects, e.g., the color image information of the G and R color regions as the reference image information, which is not used for generation of the emphasized image information (B3), from the white light image information (B1, G1, R1), and transmits this color image information (G1, R1) to the first development circuit 43.

On the other hand, at a step S3 which is executed concurrently with the processing of the step S1, the system control apparatus 11 issues an instruction to drive the second semiconductor laser 21 to the light source controller 22. This second semiconductor laser 21 emits the blue-violet laser light having an emission peak wavelength of 415 nm ($\lambda 2$) and a half value width of several nm or less. When this blue-violet laser light enters the second optical fiber 26 of the light guide 23, it is guided through the optical multiplexer 27 and the third optical fiber 28 from this first optical fiber 26 and applied to the light converter 24 as second excitation light.

When the second fluorescence substance 33 of this light converter 24 is irradiated with the blue-violet laser light, it is excited upon absorption of this blue-violet laser light and emits green fluorescence. This green fluorescence spectrum has a broad spectrum whose peak is present at a wavelength of 540 nm ($\lambda m$) and whose width is 95 nm. Further, a part of the blue-violet laser light is transmitted through the second fluorescence substance 33 without contributing to the green fluorescence. Consequently, the special light Q2 in which the green fluorescence is mixed with the part of the blue-violet laser light is emitted from the second fluorescence substance 33, and the subject 2 is irradiated with this special light Q2.

When the subject 2 is irradiated with this special light Q2, this light is applied to the surface layer blood vessel 3 which is present in the biotissue 4 within an irradiation region W of the special light Q2 in this subject 2. A part of this special light Q2 is absorbed in accordance with the absorption characteristics of the surface layer blood vessel 3 through which hemoglobin flows and the biotissue 4, e.g., a mucous membrane as shown in FIG. 8, and a remaining part of the same is scattered and reflected. Of this light, reflection light from the surface layer blood vessel 3 and the biotissue 4 enters the imaging apparatus 7.

The reflection light from the surface layer blood vessel 3 and the biotissue 4 enters this imaging apparatus 7, and the imaging apparatus 7 receives this reflection light by the B color region, the G color region, and the R color region of the CCDs and outputs three pieces of image information of BGR, i.e., the special light image information (B2, G2, R2). This special light image information (B2, G2, R2) is supplied to the image acquiring circuit 8, and stored in the second memory 41 of this circuit 8. It is to be noted that the special light image information (B2, G2, R2) is stored in the second memory 41 as three pieces of image information (B2), (G2), and (R2) of the respective colors.

Light receiving sensitivity characteristics of the B color pixels in the imaging apparatus 7 are present in the wavelength region of 380 nm to 540 nm as shown in FIG. 8, and hence the reflection light from the surface layer blood vessel 3 and the intermediate layer blood vessel 5 received by the B color pixels turns to the blue-violet laser light and the green fluorescence. That is, a color component received by the B color pixels is mainly the blue-violet laser light.

Then, at a step S4, the image arithmetic section 45 selects color information to generate the emphasized image information (B3) from the special light image information (B2, G2, R2) stored in the second memory 41, e.g., the second color image information (B2) of the B color region like the above. This image arithmetic section 45 selects, e.g., the second color image information (G2, R2) of the G and R color regions as the reference image information, which is not used for generation of the emphasized image information (B3), from the special light image information (B2, G2, R2), and transmits this special light image information (G2, R2) to the second development circuit 44.

Then, at a step S5, the image arithmetic section 45 reads out the white light image information (B1, G1, R1) stored in the first memory 40 and the special light image information (B2, G2, R2) stored in the second memory 41.

The image arithmetic section 45 selects the first color image information (B1) and the second color image information (B2) of the same wavelength region, e.g., the B color region included in each of the read white light image information (B1, G1, R1) and special light image information (B2, G2, R2).

The image arithmetic section 45 generates the emphasized image information (B3) to emphasize, e.g., the surface layer blood vessel 3 where hemoglobin is present by executing a predetermined arithmetic operation for the first color image information (B1) of the B color region and the second color image information (B2) of the same color region, and stores this emphasized image information (B3) in the third memory 46. This emphasized image information (B3) has higher contrast of the surface layer blood vessel 3 than that of the first color image information (B1) and the second color image information (B2).

A difference between the first color image information (B1) provided by the white light and the second color image information (B2) provided by the special light will now be described.

When the surface layer blood vessel 3 is displayed in the image display apparatus 9 such as a CRT or LCD display, the second color image information (B2) of this surface layer blood vessel 3 acquired by irradiating the subject 2 with the special light (at the time of emission of the blue-violet laser light) is relatively darkly displayed as compared with the first color image information (B1) of the same acquired by irradiating the subject 2 with the white light (at the time of emission of the blue laser light). That is because hemoglobin flowing through the surface layer blood vessel 3 easily absorbs the blue-violet laser light (the special light).

When the biotissue 4 is displayed in the image display apparatus 9 such as a CRT or LCD display, since the absorption characteristics of a wavelength difference between the blue-violet color laser light and the blue laser light of the biotissue 4 are smaller than the absorption characteristics of hemoglobin, an image of the biotissue 4 has a smaller luminance difference than that of an image of the surface layer blood vessel 3 in a comparison between displayed images of the second color image information (B2) and the first color image information (B1).

Thus, the contrast of the surface layer blood vessel 3 to the biotissue 4 is higher in an image based on the second color image information (B2) acquired by irradiation of the special light than in an image based on the first color image information (B1) acquired by irradiation of the white light.

Figure 9:
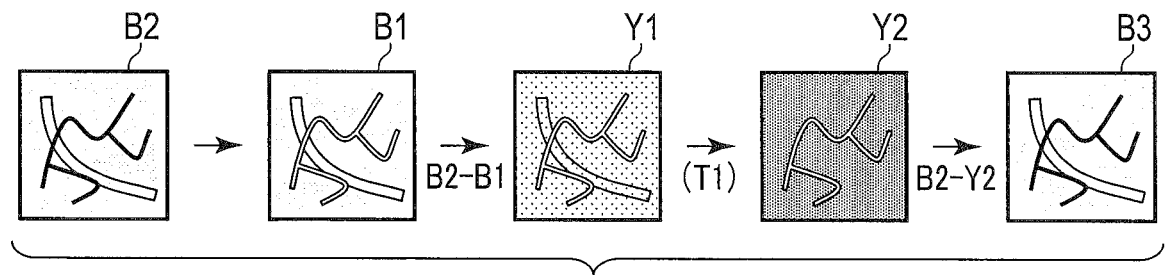
FIG. 9 is a schematic view showing a technique of generating of emphasized image information (B3) in the system.

A technique of generating the emphasized image information (B3) will now be specifically described with reference to FIG. 9.

The image arithmetic section 45 extracts difference information (first intermediate information) Y1 of the same wavelength region, i.e., difference information Y1 (=B2−B1) by executing an arithmetic operation to obtain a difference between the second color image information (B2) of the B color region in the special light image information (B2, G2, R2) and the first color image information (B1) of the B color region in the white light image information (B1, G1, R1).

The image arithmetic section 45 sets a threshold value to the difference information (Y1), and extracts absorption difference information (second intermediate information) Y2 (>T1) equal to or above the threshold value (T1) from this difference information (Y1).

The image arithmetic section 45 executes an arithmetic operation to obtain a difference between the second color image information (B2) and the extracted absorption difference information (Y2), and generates emphasized image information B3 (=B2−Y2) to emphasize, e.g., the surface layer blood vessel 3 where hemoglobin is present with increased contrast. This emphasized image information (B3) has higher contrast of the surface layer blood vessel 3 than that in the white light image information (the first color image information B1) and the special light image information (the second color image information B2).

This image arithmetic section 45 may execute an arithmetic operation to obtain a difference between the first color image information (B1) and the extracted absorption difference information (the first intermediate information) Y2, and may generate the emphasized image information (B3=B1−Y1).

Figure 10:
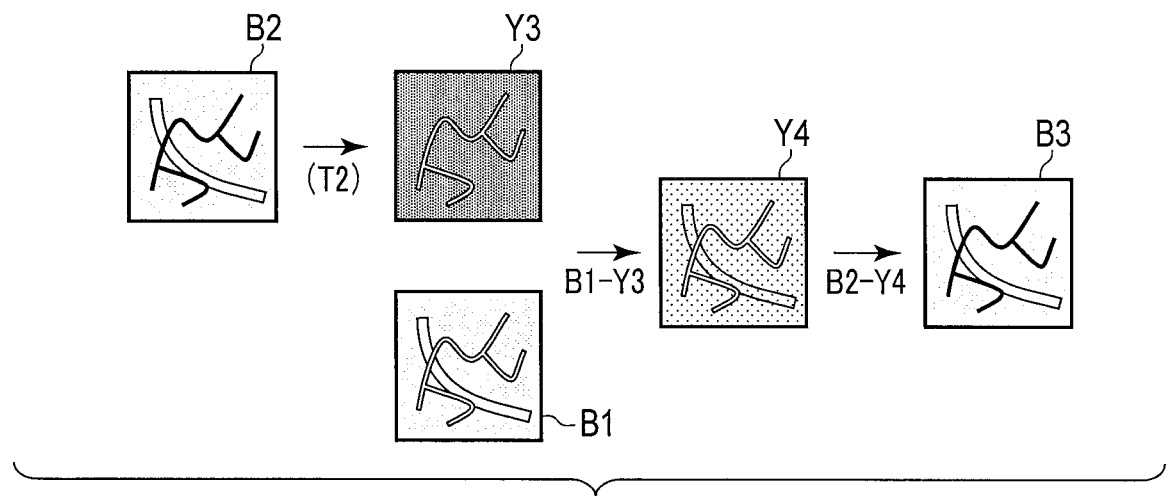
FIG. 10 is a schematic view showing another technique of generating of the emphasized image information (B3) in the system.

Another technique of generating the emphasized image information (B3) will now be specifically described with reference to FIG. 10.

The image arithmetic section 45 sets a threshold value (T2) which is an average luminance value to luminance information of the same wavelength region included in the special light image information (B2, G2, R2), e.g., the B color region, and extracts luminance information (third intermediate information) Y3 (>T2) which is equal to or above the threshold value (T2) from the second color image information (B2). The threshold value (T2) which is the average luminance value is calculated from each pixel luminance value of the second color image information (B2) having a large absorption amount of hemoglobin.

The image arithmetic section 45 executes an arithmetic operation to obtain a difference between the first color image information of the same wavelength region included in the white light image information (B1, G1, R1), e.g., the B color region and the extracted luminance information (the third intermediate information Y3, thereby acquiring luminance information (fourth intermediate information) Y4 (=B1−Y3).

The image arithmetic section 45 may execute an arithmetic operation to obtain a difference between the luminance information (B2) of the B region included in the special light image information (B2, G2, R2) and the luminance information (the fourth intermediate information) Y4, and may generate the emphasized image information (B3=B2−Y4) to emphasize, e.g., the surface layer blood vessel 3 where hemoglobin is present with increased contrast.

Even the emphasized image information (B3) generated by the another technique in this manner has higher contrast of the surface layer blood vessel 3 than that in the white light image information (the first color image information B1) and the special light image information (the second color image information B2).

Still another technique of generating the emphasized image information (B3) will now be described.

The image arithmetic section 45 executes image processing to reduce noise of the biotissue portion 4 (a predetermined threshold value or more) from two images corresponding to, e.g., the first color image information (B1) of the B color region included in the white light image information (B1, G1, R1) and the second color image information (B2) of the B region included in the special light image information (B2, G2, R2), thereby acquiring intermediate image information. Further, the image arithmetic section 45 may combine images of the intermediate image information and the second color image information (B2) of the B region to generate the emphasized image information (B3). This emphasized image information (B3) likewise has the high contrast of the surface layer blood vessel 3.

Furthermore, as yet another method, the image arithmetic section 45 executes image processing to extract a boundary (a predetermined difference in brightness or more) between the surface layer blood vessel 3 and the biotissue 4 from two images corresponding to the first color image information (B1) included in the white light image information (B1, G1, R1) and the first color image information (B2) of the B region included in the special light image information (B2, G2, R2), thereby generating an edge-extracted intermediate image. Furthermore, the image arithmetic section 45 may combine the edge-extracted intermediate image with an image of the first color image information (B2) of the B region to generate blood vessel emphasized image information (B3) showing the surface layer blood vessel 3 and the intermediate layer blood vessel 5 present in a deeper layer than this surface layer blood vessel 3 in different colors.

Then, at a step S6, the first development circuit 43 reads out the image information (G1, R1) which is a part of the white light image information (B1, G1, R1) stored in the first memory 40, and also reads out the emphasized image information (B3) stored in the third memory 46. The first development circuit 43 executes predetermined image processing to the image information (G1, R1) and the emphasized image information (B3, G1, R1) to generate emphasized image information (B3, G1, R1) of the white light, and outputs a white color video signal of this white light emphasized image information (B3, G1, R1). The white color video signal of this white light emphasized image information (B3, G1, R1) is transmitted to the image display apparatus 9.

Subsequently, at a step S7, this image display apparatus 9 receives the white color video signal output from the first development circuit 43, processes this white color video signal into a display signal, and displays an image of the white light emphasized image information (B3, G1, R1) in the display such as CRT or LCD.

On the other hand, at a step S8, the second development circuit 44 reads out the image information (G2) which is a part of the special image information (B2, G2, R2) stored in the second memory 41, and also reads out the emphasized image information (B3) stored in the third memory 46. The second development circuit 44 executes predetermined image processing to the image information (G2) and the emphasized image information (B3) to generate emphasized image information (B3, G2) of the special light, and outputs a special color video signal of this special light emphasized image information (B3, G2). The video signal of this special light emphasized image information (B3, G2) is transmitted to the image display apparatus 9.

Then, at a step S9, this image display apparatus 9 receives the special color video signal output from the second development circuit 44, processes this special color video signal into a display signal, and displays an image of the special light emphasized image information (B3, G2) in the display such as CRT or LCD.

The first development circuit 43 generates a white light normal observation image from the white light image information (B1, G1, R1), and outputs a white color video signal of this white light normal observation image (B1, G1, R1).

The image display apparatus 9 receives the white color video signal output from the first development circuit 43, processes this white color video signal into a display signal, and displays a white light normal observation image (B1, G1, R1) in the display such as CRT or LCD.

The second development circuit 44 generates special light normal observation image information (B2, G2) from image information (B2, G2) which is a part of the special light image information (B2, G2, R2), and outputs a special color video signal of this special light normal observation information (B2, G2).

The image display apparatus 9 receives the special color video signal output from the second development circuit 44, processes this special color video signal into a display signal, and displays an image of the special light normal observation image information (B2, G2) in the display such as CRT or LCD.

The second development circuit 44 may execute predetermined image processing to the image information (R2) which is a part of the special light image information (B2, G2, R2) stored in the second memory 41 and the emphasized image information (B3) stored in the third memory 46 to generate special light emphasized image information (B3, R2), and may output a special color video signal of this special light emphasized image information (B3, R2). Consequently, the image display apparatus 9 displays an image of the special light emphasized image information (B3, R2) in the display such as CRT or LCD.

As described above, the second development circuit 44 generates the special light emphasized observation information (B3, G2) and the special light normal observation information (B2, G2). The first development circuit 43 generates the white light emphasized observation information (B3, G1, R1) and the white light normal observation information (B1, G1, R1). At the time of this generation, the first development circuit 43 and the second development circuit 44 perform any other image processing, e.g., noise reduction, structure emphasis, color conversion, and others required for image generation by using a white balance coefficient, a color conversion coefficient, and others.

Furthermore, the first development circuit 43 is applied to various kinds of image processing on the basis of an observation mode color adjustment parameter to uniformize hues of the white light emphasized observation image (B3, G1, R1) and the white light normal observation image (B1, G1, R1).

Likewise, the second development circuit 44 stores the observation mode color adjustment parameter to uniformize hues of the special light emphasized observation image (B3, R2) and the special light normal observation image (B2, G2), and the observation mode color adjustment parameter is applied to various kinds of image processing.

With the above-described operations, two types of illumination lights, i.e., the first illumination light Q1 which is the white light and the second illumination light Q2 which is the special light can be applied to the subject 2 to acquire the white light emphasized image information (B3, G1, R1) and the special light emphasized image information (B3, G2) which enable emphasizing the blood vessel with higher contrast than that in the white light normal observation information (B1, G1, R1) and the special light normal observation information (B2, G2).

Figure 11:
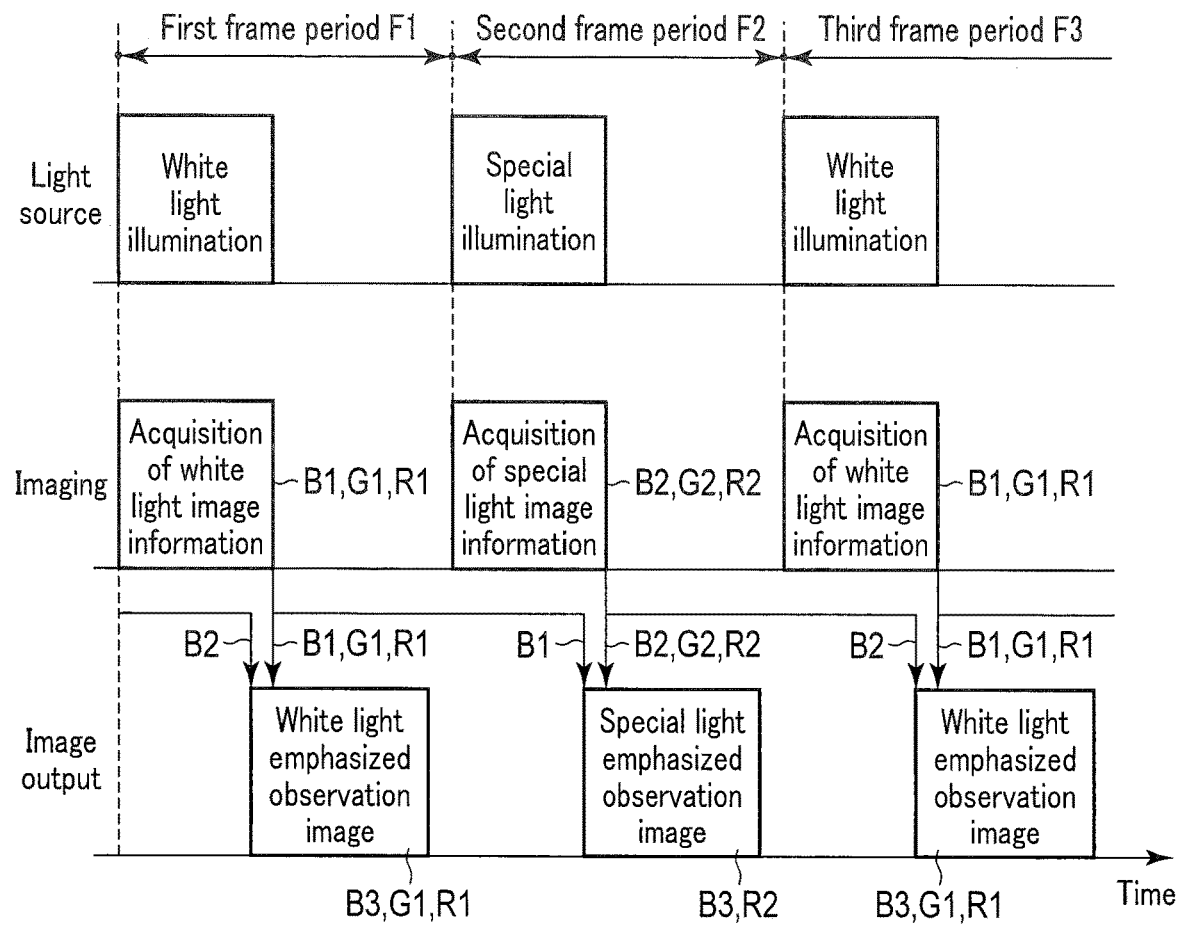
FIG. 11 is an operation timing chart at the time of alternately displaying a white light emphasized observation image and a special light emphasized observation image in the system.

An operation timing to alternately display the white light emphasized image information (B3, G1, R1) and the special light emphasized image information (B3, G2) will now be described with reference to FIG. 11.

When the blue laser light is emitted from the first semiconductor laser 20, the subject 2 is irradiated with the white light Q1 from the light converter 24.

When the blue-violet laser light is emitted from the second semiconductor laser 21, the subject 2 is irradiated with the special light Q2, which is provided by mixing the blue-violet laser light with the green fluorescence, from the light converter 24.

The white light Q1 and special light Q2 are switched in every frame period, and alternately applied to the subject 2. FIG. 11 shows first to third frame periods.

During the first frame period F1, the white light Q1 is applied to the subject 2, and the white light image information (B1, G1, R1) is acquired by imaging of the imaging apparatus 7.

During a frame period which precedes this first frame period F1, the special light Q2 has already been applied to the subject 2, and the special light image information (B2, G2, R2) has been acquired by imaging of the imaging apparatus 7.

During the previous frame period, the emphasized image information generating circuit 42 selects the first color image information (B1) and the second color image information (B2) of the same wavelength region, e.g., the B color region included in each of the white light image information (B1, G1, R1) and the special light image information (B2, G2, R2). The emphasized image information generating circuit 42 executes a predetermined arithmetic operation for the first color image information (B1) and the second color image information (B2), and thereby generates the emphasized image information (B3) to emphasize, e.g., the surface layer blood vessel 3 in which hemoglobin is present with high contrast.

Thus, during the first frame period F1, the white light emphasized image information (B3, G1, R1) is generated by an arithmetic operation for the emphasized image information (B3) acquired during the previous frame period and the white light image information (B1, G1, R1) acquired during this frame period F1.

Then, during the second frame period F2, the special light Q2 is applied to the subject 2, and the special light image information (B2, G2, R2) is acquired by imaging of the imaging apparatus 7.

During the frame period F1 which precedes this second frame period F2, the white light Q1 is applied to the subject 2 as described above, and the white light image information (B1, G1, R1) is acquired by imaging of the imaging apparatus 7.

During the second frame period F2, the emphasized image information generating circuit 42 selects the first color image information (B1) and the second color image information (B2) of the B color region included in each of the white light image information (B1, G1, R1) and the special light image information (B2, G2, R2). The emphasized image information generating circuit 42 executes a predetermined arithmetic operation for the first color image information (B1) and second color image information (B2), and thereby generates the emphasized image information (B3) to emphasize, e.g., the surface layer blood vessel 3 in which hemoglobin is present with high contrast.

Thus, during the second frame period F2, the special light emphasized image information (B3, G2, R2) is generated by an arithmetic operation for the special light image information (B2, G2, R2) and the emphasized image information (B3).

Thereafter, the white light Q1 and the special light Q2 are switched in every frame period and alternately applied to the subject 2, whereby the white light observation emphasized image (B3, G1, R1) and the special light observation emphasized image (B3, G2, R2) are alternately generated in every frame period.

As described above, according to the first embodiment, the absorption characteristics of hemoglobin present in the subject 2 are taken into consideration, the first color image information (B1) and the second color image information (B2) of the same wavelength region, e.g., the B color region included in each of the white light image information (B1, G1, R1) and the special light image information (B2, G2, R2) are selected, the predetermined arithmetic operation is executed for this first color image information (B1) and second color image information (B2), and thereby the emphasized image information (B3) to emphasize, e.g., the surface layer blood vessel 3 in which the target substance such as hemoglobin is present is generated. Consequently, the contrast of the surface layer blood vessel 3 can be increased beyond those in the white light image information (B1, G1, R1) and the special light image information (B2, G2, R2). An image of the emphasized image information (B3) having the increased contrast of the surface layer blood vessel 3 can be displayed in the image display apparatus 9 which is a display such as CRT or LCD.

In particular, since the white light Q1 and the special light Q2 which are different in absorption to the target substance such as hemoglobin are applied to the target substance to acquire the white light image information (B1, G1, R1) and the special light image information (B2, G2, R2) and the predetermined arithmetic operation is performed for these pieces of information (B1, G1, R1) and (B2, G2, R2), the emphasized image information (B3) having less image noise and a high SN ratio can be acquired.

The biotissue 4 has smaller absorption characteristics of a wavelength difference between the blue-violet laser light and the blue laser light than the absorption characteristics of hemoglobin. Consequently, an image of the biotissue 4 has a smaller difference in luminance than that in an image of the surface layer blood vessel 3, and the contrast of the surface layer blood vessel 3 based on the second color image information (B2) acquired by irradiation of the special light can be increased beyond the contrast of the surface layer blood vessel 3 based on the first color image information (B1) acquired by irradiation of the white light.

As a technique for generating the emphasized image information (B3), difference information Y1 between the special light image information (B2) of the B color region and the white light image information (B1) of the same B color region is extracted, absorption difference information Y2 equal to or above a threshold value is extracted from this difference information Y1, and the emphasized image information (B3) to emphasize, e.g., the surface layer blood vessel 3 in which hemoglobin is present with high contrast is generated from a difference between this absorption difference information Y2 and the special light image information (B2).

As another technique, the luminance information (Y3) equal to or above a threshold value is extracted from the luminance information of, e.g., the B color region included in the special light image information (B2, G2, R2), luminance information (Y4) of a difference between this luminance information (Y3) and the luminance information (B1) of the B color region is acquired, and the emphasized image information (B3) to emphasize, e.g., the surface layer blood vessel 3 in which hemoglobin is present is generated from the difference between this luminance information (Y4) and the luminance information (B2) of the B region.

As the emphasized image information (B3) generated by these techniques, it is possible to obtain the emphasized image information (B3) to emphasize the surface layer blood vessel 3 with higher contrast than that in a normal image generated from single illumination light. When this emphasized image information (B3) is displayed in the image display apparatus 9 which is the display such as CRT or, the surface layer blood vessel 3 can be readily identified and effective for a diagnosis.

Since the white light normal observation image (B1, G1, R1) can be generated by the first development circuit 43 and the special light normal observation image information (B2, G2) can be generated by the second development circuit 44, the white light normal observation image (B1, G1, R1) and the special light normal observation image information (B2, G2) can be displayed in the image display apparatus 9 at a desired timing in accordance with conditions of the observation mode by controlling display timing of the generated white light normal observation image (B1, G1, R1) and special light normal observation image information (B2, G2).

Since the image acquiring circuit 8 generates the white light emphasized image information (B3, G1, R1) on the basis of the emphasized image information (B3) and the white light image information (B1, G1, R1), solely the surface layer blood vessel 3 in which the target substance such as hemoglobin flows can be emphasized with high contrast while a hue of the observation target, e.g., the subject 2 keeps conditions of the while light image information (B1, G1, R1) by this white light emphasized image information (B3, G1, R1).

The white light emphasized image (B3, G1, R1) enables emphasizing the target substance, e.g., the surface layer blood vessel 3 in which hemoglobin or the like flows with high contrast without losing the white light image information (B1, G1, R1) of a non-target substance such as mucous membrane.

It is to be noted that the first embodiment may be modified as follows.

Figure 12:
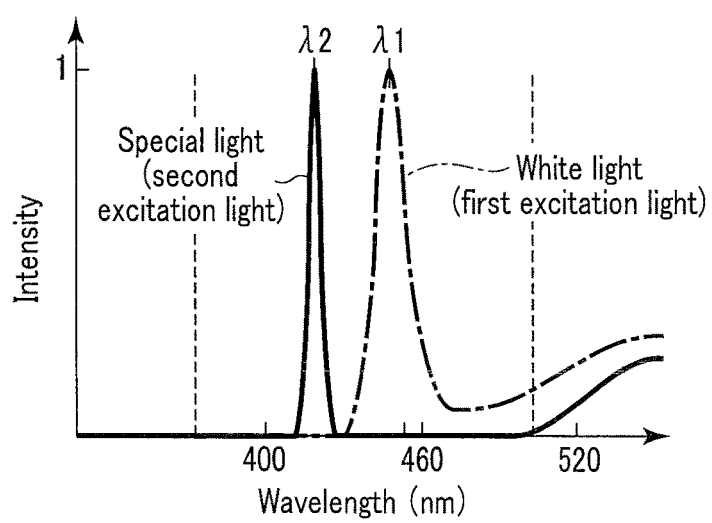
FIG. 12 is a view showing intensities of white light and special light to wavelengths when illumination light is generated by using a blue LED in the system.

Although the white light Q1 is generated by using the blue laser in the first embodiment, a spectrum of the white light, namely, the white light Q1 having a spectral component from the blue region to the green region may be generated by using blue LED light emitted from a blue light emitting diode (LED). FIG. 12 shows intensities of the white light Q1 and the special light Q2 to wavelengths when the illumination light is generated by using the blue LED.

Although the special light Q2 is generated by using the blue-violet laser having a wavelength of 415 nm, it may be generated by using the blue-violet laser having a wavelength region of 400 nm to 435 nm whose hemoglobin absorption characteristics are approximately double the counterpart of the wavelength 450 nm of the blue laser which is used for generation of the white light Q1.

As a fluorescence substance mounted in the light converter 24, a green fluorescence substance or a red fluorescence substance which can be excited by blue fluorescence may be used. The green fluorescence substance or the red fluorescence substance could be mounted in the light converter 24 under concentration conditions which enable emission of the white light when the blue light enters the light converter 24.

The image acquiring circuit 8 may generate the white light normal observation image (B1, G1, R1) or/and the special light normal observation image information (B2, G2), and align and display the white light normal observation image (B1, G1, R1) or/and the special light normal observation image information (B2, G2) and the white light emphasized image information (B3, G1, R1) or/and the special light emphasized image information (B3, G2) in the image displaying apparatus 9 such as a monitor.

Besides alternately repeatedly generating the white light emphasized observation image (B3, G1, R1) and the special light emphasized observation image (B3, G2), the white light Q1 and the special light Q2 may be applied to display an emphasized observation image under predetermined timing conditions alone by a setting method of the observation mode input apparatus 10.

Second Embodiment

A second embodiment according to the present invention will now be described hereinafter with reference to the drawings. It is to be noted that like reference numerals denote parts equal to those in FIG. 1 to omit a detailed description thereof.

Figure 13:
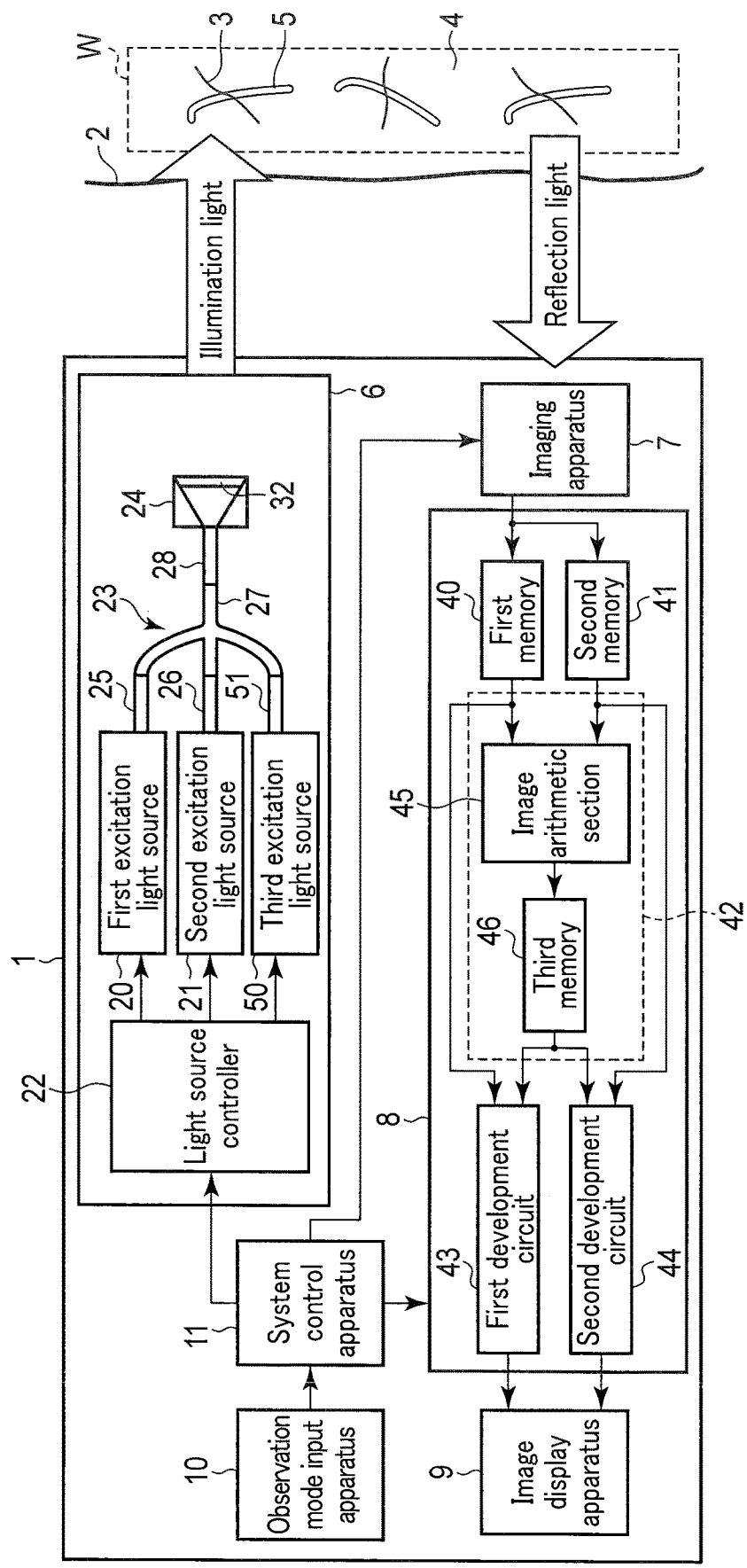
FIG. 13 is a block diagram showing a second embodiment of the observation image acquiring system according to the present invention.

FIG. 13 shows a block diagram of an observation image acquiring system 1. A light source apparatus 6 applies first light (first illumination light) Q1 and special light Q3 which is mixed light of a blue-violet laser light and a green laser light to a subject 2. As described above, the light source apparatus 6 includes a first excitation light source 20 including a first semiconductor laser (LD) which emits the blue laser light, a second excitation light source 21 including a second semiconductor laser (LD) which emits the blue-violet laser light, a light source controller 22, a light guide 23, and a light converter 24, and further includes a third excitation light source 50.

The third excitation light source 50 includes a third semiconductor laser (LD) which emits the green laser light having an emission peak wavelength of 540 nm. The third semiconductor laser (LD) will be referred to as a third semiconductor laser 50 hereinafter.

The light converter 24 is excited by the blue laser light exiting from a third optical fiber 28, and performs wavelength conversion to provide the white light Q1.

This light converter 24 is hardly excited by irradiation of the mixed light of the blue-violet laser light and the green laser light, and emits the blue-violet laser light and the green laser light transmitted therethrough as the special light Q3.

This light converter 24 includes a holder 30, a glass member 31 as a light transmitter, and a first fluorescence substance 32 as a first wavelength converter. The second fluorescence substance 33 is eliminated from the light converter 24 in the first embodiment, and the light converter 24 has the first fluorescence substance 32 alone mounted therein. The first fluorescence substance 32 absorbs the blue laser light emitted from the first semiconductor laser 20, and emits yellow fluorescence. Even if the green laser light emitted from the third semiconductor laser 50 is applied, this first fluorescence substance 32 transmits the green laser light therethrough, and it is not excited.

When the white light Q1 is applied to an observation target, e.g., the subject 2, the imaging apparatus 7 acquires white light image information (B1, G1, R1) as first image information in accordance with each pixel region, i.e., a B color region, a G color region, or an R color region. This white light image information (B1, G1, R1) is stored in a first memory 40.

When the special light Q3 is applied to the subject 2, the imaging apparatus 7 acquires special light image information (B4, G4, R4) as third image information in accordance with each pixel region i.e., the B color region, the G color region, or the R color region. The special light image information (B4, G4, R4) is stored in the second memory 41.

An emphasized image information generating circuit 42 generates emphasized image information (B3) to emphasize, e.g., a surface layer blood vessel 3 in which hemoglobin as a target substance is present with high contrast on the basis of the white light image information (B1, G1, R1) stored in the first memory and the special light image information (B4, G4, R4) stored in the second memory 41.

Specifically, an image arithmetic section 45 of the emphasized image information generating circuit 42 selects first color image information (B1) and second color image information (B4) in the same wavelength region, e.g., the B color region included in each of the white light image information (B1, G1, R1) and the special light image information (B4, G4, R4), as reference image information for emphasized image information generation. The image arithmetic section 45 executes a predetermined arithmetic operation for this first color image information (B1) and second color image information (B4) to generate the emphasized image information (B3) which realizes emphasizing, e.g., the surface layer blood vessel 3 in which hemoglobin is present with high contrast.

This image arithmetic section 45 stores the generated emphasized image information (B3) in a third memory 46. This emphasized image information (B3) has higher contrast of the surface layer blood vessel 3 than that of the white light image information (B1, G1, R1) and the special light image information (B4, G4, R4).

The image arithmetic section 45 selects the first color image information (G1) and the second color image information (G4) of the same wavelength region, e.g., the G color region included in each of the white light image information (B1, G1, R1) and the special light image information (B4, G4, R4). The image arithmetic section 45 executes a predetermined arithmetic operation for this first color image information (G1) and second color image information (G4) to generate emphasized image information (G5) which realizes emphasizing, e.g., an intermediate layer blood vessel 5 in which hemoglobin is present with high contrast.

This image arithmetic section 45 stores the generated emphasized image information (G5) in the third memory 46. This emphasized image information (G5) has higher contrast of the intermediate layer blood vessel 5 than that of the white light image information (B1, g1, R1).

A first development circuit 43 executes predetermined image processing to the image information (R1) which is a part of the white light image information (B1, G1, R1) stored in the first memory 40, the emphasized image information (B3) stored in the third memory 46, and the emphasized image information (G5) stored in the third memory 46 to generate white light emphasized image information (B3, G5, R1), and outputs a white light color video signal of this white light emphasized image information (B3, G5, R1).

A second development circuit 44 executes predetermined image processing to the emphasized image information (B3) stored in the third memory 46 and the emphasized image information (G5) stored in the third memory 46 to generate special light emphasized image information (B3, G5), and outputs a special light color video signal of this special light emphasized image information (B3, G5).

An image display apparatus 9 receives a video signal of a white light emphasized observation image (B3, G5, R1) output from the first development circuit 43, and displays its image in a display such as CRT or LCD.

The image display apparatus 9 receives a video signal of the special light emphasized observation image (B3, G5), and displays an image of this signal in the display.

An operation of the thus configured system 1 will now be described.

The first semiconductor laser 20 emits the blue laser light. This blue laser light is guided by a light guide 23, and applied to the light converter 24. The first fluorescence substance 32 of this light converter 24 emits the yellow fluorescence upon being irradiated with the blue laser light, transmits a part of the blue laser light therethrough, and emits the white light Q1 in which the yellow fluorescence is mixed with a part of the blue laser light. This white light Q1 is applied to the subject 2.

Reflection light from the surface layer blood vessel 3 and biotissue 4 enters the imaging apparatus 7, and the imaging apparatus 7 receives this reflection light by the B color region, the G color region, and the R color region of CCDs and outputs the white light image information (B1, G1, R1). This white light image information (B1, G1, R1) is stored in the first memory 40.

The image arithmetic section 45 of the emphasized image information generating circuit 42 selects, e.g., the first color image information (B1) of the B color region from the white light image information (B1, G1, R1) stored in the first memory 40.

On the other hand, the second semiconductor laser 21 emits the blue-violet laser light. In addition to this, the third semiconductor laser 50 emits the green laser light. Mixed light of the blue-violet laser light and the green laser light is guided by the light guide 23, and applied to the light converter 24.

The first fluorescence substance 32 of this light converter 24 is hardly excited even if it is irradiated with the blue-violet laser light emitted from the second semiconductor laser 21 and the green laser light emitted from the third semiconductor laser 50. Consequently, components of the blue-violet laser light and the green laser light are transmitted through this substance, and applied to the subject 2 as the special light Q3.

When the special light Q3 is applied to the subject 2, the imaging apparatus 7 acquires special light image information (B4, G4, R4) of each of the pixel regions, i.e., the B color region, the G color region, and the R color region. This special light image information (B4, G4, R4) is stored in the second memory 41.

The emphasized image information generating circuit 42 generates the emphasized image information (B3) to emphasize, e.g., the surface layer blood vessel 3 in which hemoglobin as the target substance is present with high contrast on the basis of the white light image information (B1, G1, R1) stored in the first memory 40 and the special light image information (B4, G4, R4) stored in the second memory 41.

Specifically, the image arithmetic section 45 of the emphasized image information generating circuit 42 selects the first color image information (B1) and the second color image information (B4) of the same wavelength region, e.g., the B color region included in each of the white light image information (B1, G1, R1) and the special light image information (B4, G4, R4). The image arithmetic section 45 executes a predetermined arithmetic operation for this first color image information (B1) and second color image information (B4), and thereby generates the emphasized image information (B3) which realizes emphasizing, e.g., the surface layer blood vessel 3 in which hemoglobin is present with high contrast. This image arithmetic section 45 stores the generated emphasized image information (B3) in the third memory 46. This emphasized image information (B3) has higher contrast of the surface layer blood vessel 3 than that of the white light image information (B1, G1, R1) and the special light image information (B4, G4, R4).

The image arithmetic section 45 selects the first color image information (G1) and the second color image information (G4) of the same wavelength region, e.g., the G color region included in each of the white light image information (B1, G1, R1) and the special light image information (B4, G4, R4). The image arithmetic section 45 executes a predetermined arithmetic operation for this first color image information (G1) and second color image information (G4) to generate the emphasized image information (G5) which realizes emphasizing, e.g., the intermediate layer blood vessel 5 in which hemoglobin is present with high contrast. This image arithmetic section 45 stores the generated emphasized image information (G5) in the third memory 46. This emphasized image information (G5) has higher contrast of the intermediate layer blood vessel 5 than that of the white light image information (B1, G1, R1) and the special light image information (B4, G4, R4).

The first development circuit 43 executes predetermined image processing to the image information (R1) which is a part of the white light image information (B1, G1, R1) stored in the first memory 40, the emphasized image information (B3) stored in the third memory 46, and the emphasized image information (G5) stored in the third memory 46 to generate white light emphasized image information (B3, G5, R1), and outputs a white color video signal of this white light emphasized image information (B3, G5, R1).

The image display apparatus 9 receives the white color video signal of a white light emphasized observation image (B3, G5, R1) output from the first development circuit 43, and displays its image in the display such as CRT or LCD.

The second development circuit 44 executes predetermined processing to the emphasized image information (B3) stored in the third memory 46 and the emphasized image information (G5) stored in the third memory 46 to generate special light emphasized image information (B3, G5), and outputs a special color video signal of this special light emphasized image information (B3, G5).

The image display apparatus 9 receives the special color video signal of the special light emphasized observation image (B3, G5), and displays its image in the display.

As described above, according to the second embodiment, the third semiconductor laser 50 which emits the green laser light having the emission peak wavelength of 540 nm is provided, the absorption characteristics of hemoglobin which is present in the subject 2 are taken into consideration and, in addition to the generation of the emphasized image information (B3) to emphasize the surface layer blood vessel 3 with high contrast, the emphasized image information (G5) to emphasize, e.g., the intermediate layer blood vessel 5 in which the target substance such as hemoglobin is present with high contrast is generated by selecting the color image information (G1) and the color image information (G4) of the same wavelength region, e.g., the G color region included in each of the white light image information (B1, G1, R1) and the special light image information (B4, G4, R4) and executing the predetermined arithmetic operation. Consequently, the contrast of the intermediate layer blood vessel 5 can be increased beyond the counterparts of the white light image information (B1, G1, R1) and the special light image information (B4, G4, R4). An image of the emphasized image information (G5) with the increased contrast of the intermediate layer blood vessel 5, i.e., images of the white light emphasized image information (B3, G5, R1) and the special light emphasized image information (B3, G5, R1) can be displayed in the image display apparatus 9 which is a display such as CRT or LCD.

In addition, the first development circuit 43 may be configured to output a video signal of the white light normal observation image (B1, G1, R1) like the above example. In this white light normal observation image (B1, G1, R1), the contrast of the surface layer blood vessel 3 can be increased, and an image of the emphasized image information with the increased contrast of the surface layer blood vessel 3 can be displayed in the image display apparatus 9 which is the display such as CRT or LCD.

The second development circuit 44 may execute predetermined image processing to the image information (B4) which is a part of the special light image information (B4, G4, R4) stored in the second memory 41 and the emphasized image information (G5) stored in the third memory 46, and output a video signal of the emphasized image information (B4, G5) of the special light. When this special light emphasized image information (B4, G5) is adopted, an image of the emphasized image information (B5) with the increased contrast of the intermediate blood vessel 5 can be displayed in the image display apparatus 9.

It is to be noted that the second embodiment may be modified as follows.

In this embodiment, the emphasized image information (G5) is generated from the color image information (G1) and the color image information (G4) of the same wavelength region, e.g., the G color region included in each of the white light image information (B1, G1, R1) and the special light image information (B4, G4, R4). Consequently, the thus generated emphasized image information (G5) may be displayed in the image display apparatus 9 which is the display such as CRT or LCD. With the emphasized image information (G5), an image having, e.g., the intermediate layer blood vessel 5, in which the target substance such as hemoglobin is present, emphasized therein with high contrast can be observed.

The second development circuit 44 may execute predetermined image processing to the image information (B4) which is a part of the special light image information (B4, G4, R4) stored in the second memory 41 and the emphasized image information (G5) stored in the third memory 46 to generate the special light emphasized image information (B4, G5), and output a special color video signal of this special light emphasized image information (B4, G5). With this special light normal observation image (B4, G5), an image of the emphasized image information (G5) with the increased contrast of the intermediate layer blood vessel 5 can be displayed in the image display apparatus 9.

This second development circuit 44 may generate image information (B4, G4) which is a part of the special light image information (B4, G4, R4), and output a special color video signal of this special light normal observation image (B4, G4).

Thus, according to the second embodiment, an image of the emphasized image information of the surface layer blood vessel 3 and the intermediate layer blood vessel 5 or the intermediate layer 5 alone having the increased contrast can be displayed in the image display apparatus 9 which is the display such as CRT or LCD.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An observation image acquiring system comprising:
a light source configured to irradiate an observation target with first light in a wavelength region which does not include a wavelength region where an absorption peak of a target substance included in the observation target is present and second light in a wavelength region where the absorption peak is present;
an image sensor configured to image the observation target irradiated with the first light or the second light to acquire image information; and
a processor comprising hardware, wherein the processor is configured to perform an arithmetic operation for the image information acquired by the image sensor to generate emphasized image information which emphasizes the target substance,
wherein the processor is configured to:
extract absorption difference information indicating a difference of absorption of the target substance between first image information acquired by the image sensor when the observation target is irradiated with the first light and second image information acquired by the image sensor when the observation target is irradiated with the second light, wherein a period that the observation target is irradiated with the second light is different from a period that the observation target is irradiated with the first light; and
add the absorption difference information to the second image information to generate the emphasized image information.

2. The observation image acquiring system according to claim 1, wherein the processor is configured to:
: select first color image information and second color image information of a same wavelength region included in both the first image information and the second image information; and
: extract the absorption difference information between the first color image information and the second color image information to generate the emphasized image information which emphasizes the target substance.

3. The observation image acquiring system according to claim 1,
wherein the processor is configured to generate the emphasized image information having higher contrast of the target substance than contrasts in the first image information and the second image information.

4. The observation image acquiring system according to claim 1,
wherein a peak wavelength of the second light is present in a wavelength region closer to an absorption peak of the target substance than a peak wavelength of the first light, and
wherein, when the wavelength region which corresponds to a wavelength region where the absorption peak of the target substance is present and has maximum light receiving sensitivity among respective wavelength regions of the image sensor is a specific color region, an emission spectral component of the second light in the specific color region has an intensity equal to or above that of an emission spectral component of the first light.

5. The observation image acquiring system according to claim 4,
wherein the first and second lights have different bandwidths of emission spectrums in the specific color region.

6. The observation image acquiring system according to claim 4,
wherein the first and second lights have emission spectrums which do not overlap each other in the specific color region.

7. The observation image acquiring system according to claim 1,
wherein the processor is configured to perform at least one of:
: generate white light emphasized image information by using the emphasized image information generated and a part of the first image information; and
: generate special light emphasized image information by using the emphasized image information generated and a part of the second image information.

8. The observation image acquiring system according to claim 1,
wherein the first light is white light,
wherein the image sensor is configured to acquire white light image information as the first image information when the observation target is irradiated with the white light, and
wherein the processor is configured to generate white light emphasized image information on the basis of the emphasized image information and the white light image information.

9. The observation image acquiring system according to claim 1,
wherein the second light is special light to emphasize the target substance,
wherein the image sensor is configured to acquire special light image information as the second image information when the observation target is irradiated with the special light, and
wherein the processor is configured to generate special light emphasized image information on the basis of the emphasized image information and the special light image information.

10. The observation image acquiring system according to claim 1,
wherein the image sensor comprises a pixel region comprising a blue region, a pixel region comprising a green region, and a pixel region comprising a red region, and
wherein the processor is configured to:
: acquire the first image information in accordance with each of pixel regions when the observation target is irradiated with the first light, and acquire the second image information in accordance with each of the pixel regions when the observation target is irradiated with the second light;
: select the first image information and second image information of a same wavelength region included in each of the first image information and second image information; and
: extract the absorption difference information between the first image information and second image information to generate the emphasized image information.

11. The observation image acquiring system according to claim 1,
wherein the processor is configured to:
: extract absorption difference information indicative of a difference in absorption of the target substance from the first image information and the second image information; and
: add the absorption difference information to the second image information having the stronger absorption of the target substance to generate the emphasized image information.

12. The observation image acquiring system according to claim 11,
wherein the first light is white light containing spectral components in a blue region, a green region, and a red region,
wherein the second light is special light containing spectral components in the blue region and the green region,
wherein the image sensor is configured to:
: acquire the first image information when the observation target is irradiated with the white light; and
: acquire the second image information when the observation target is irradiated with the special light, and
wherein the processor is configured to:
: extract difference information by executing an arithmetic operation to obtain a difference between the first and second image information of a same wavelength region;
: extract absorption difference information which is equal to or above a threshold value from the difference information; and
: generate the emphasized image information by executing an arithmetic operation to obtain a difference between the extracted absorption difference information and image information which is one of the first and second image information of the same wavelength region.

13. The observation image acquiring system according to claim 12,
wherein the same wavelength region is the blue region.

14. The observation image acquiring system according to claim 1,
wherein the processor is configured to:
execute image noise reduction processing only to image information other than the target substance from the first image information and the second image information; and
generate the emphasized image information from the image information subjected to the image noise reduction processing.

15. The observation image acquiring system according to claim 14,
wherein the first light is white light containing spectral components in a blue region, a green region, and a red region,
wherein the second light is special light containing spectral components in the blue region and the green region,
wherein the image sensor is configured to:
acquire the first image information when the observation target is irradiated with the white light; and
acquire the second image information when the observation target is irradiated with the special light, and
wherein the processor is configured to:
extract luminance information equal to or above a threshold value from luminance information of a same wavelength region included in the second image information;
acquire difference information by executing an arithmetic operation to obtain a difference between luminance information of the same wavelength region included in the first image information and the extracted luminance information; and
generate the emphasized image information by executing an arithmetic operation to obtain a difference between luminance information of the same wavelength region included in the second image information and the difference information.

16. The observation image acquiring system according to claim 1,
wherein assuming that the wavelength region which corresponds to a wavelength region where an absorption peak of the target substance is present and which has maximum light receiving sensitivity in respective wavelength regions of the image sensor is a specific color region,
wherein the light source comprises:
a first semiconductor laser configured to emit a first emission spectrum including a first peak wavelength in a blue region included in the specific color region;
a second semiconductor laser configured to emit a second emission spectrum including a second peak wavelength in a blue-violet region included in the specific color region; and
a wavelength convertor configured to:
absorb a part of the first emission spectrum emitted from the first semiconductor laser to emit a broad fluorescence spectrum including a green region and a red region, and irradiate the observation target with mixed light of the fluorescence spectrum and the first emission spectrum as the first light; and
irradiate the observation target with the second emission spectrum as the second light.

17. The observation image acquiring system according to claim 16,
wherein the first semiconductor laser is configured to emit the first emission spectrum having a first peak wavelength in a wavelength region of 440 nm to 460 nm included in the blue region, and
wherein the second semiconductor laser is configured to emit the second emission spectrum having a second peak wavelength in a wavelength region of 400 nm to 440 nm included in the blue-violet region.

18. The observation image acquiring system according to claim 1,
wherein the first light is white light containing spectral components in a blue region, a green region, and a red region,
wherein the second light is special light containing spectral components in the blue region and the green region,
wherein the image sensor is configured to:
acquire the first image information when the observation target is irradiated with the white light; and
acquire the second image information when the observation target is irradiated with the special light, and
wherein the processor is configured to:
configure first observation image information which is a predetermined color image by executing an arithmetic operation for the emphasized image information and one of pieces of image information of the blue region, the green region, and the red region included in the first image information; and
configure second observation image information which is a predetermined color image by executing an arithmetic operation for the emphasized image information and one of pieces of image information of the blue region and the green region included in the second image information.

19. The observation image acquiring system according to claim 1,
wherein the light source is configured to repeatedly apply the first light and the second light to the observation target,
wherein the image sensor is configured to:
acquire a first frame image as the first image information every time the first light is applied to the observation target; and
acquire a second frame image as the second image information every time the second light is applied to the observation target, and
wherein the processor is configured to:
generate first emphasized image information which is emphasized-image information concerning the first light and second emphasized image information which is emphasized-image information concerning the second light on the basis of the first frame image and the second frame image which are repeatedly acquired by the image sensor;
sequentially configures first observation image information on the basis of the first emphasized image information; and
sequentially configures second observation image information on the basis of the second emphasized image information.

20. An observation image acquiring system comprising:
a light source configured to irradiate an observation target with first light in a wavelength region which does not include a wavelength region where an absorption peak of a target substance included in the observation target is present and second light in a wavelength region where the absorption peak is present;

an image sensor configured to image the observation target to acquire image information; and a processor comprising hardware, wherein the processor is configured to perform an arithmetic operation for the image information acquired by the image sensor to generate emphasized image information which emphasizes the target substance, wherein the processor is configured to:
    generate the emphasized image information on the basis of first image information acquired by the image sensor when the observation target is irradiated with the first light and second image information acquired by the image sensor when the observation target is irradiated with the second light, wherein a period that the observation target is irradiated with the second light is different to a period that the observation target is irradiated with the first light, wherein a peak wavelength of the second light is present in a wavelength region closer to an absorption peak of the target substance than a peak wavelength of the first light, wherein, when the wavelength region which corresponds to a wavelength region where the absorption peak of the target substance is present and has maximum light receiving sensitivity among respective wavelength regions of the image sensor is a specific color region, an emission spectral component of the second light in the specific color region has an intensity equal to or above that of an emission spectral component of the first light, wherein the light source comprises:
    a first semiconductor laser configured to emit a blue laser light in a blue region included in the specific color region;
    a second semiconductor laser configured to emit a blue-violet laser light in a blue-violet region included in the specific color region;
    a third semiconductor laser configured to emit a green laser light in a green region included in the specific color region; and
    a wavelength converter configured to:
        be excited by the blue laser light to perform wavelength conversion into white light; and
        perform wavelength conversion into special light by irradiation of mixed light of the blue-violet laser light and the green laser light, wherein the image sensor comprises a pixel region including a blue region, a pixel region including a green region, and a pixel region including a red region, wherein the image sensor is configured to:
    acquire white light image information as the first image information in accordance with each of pixel regions when the observation target is irradiated with the white light; and
    acquire special light image information as the second image information in accordance with each of the pixel regions when the observation target is irradiated with the special light, and wherein the processor is configured to:
    select the first and second image information of at least the green region which is a same wavelength region included in the white light image information and the special light image information; and
    generate respective pieces of emphasized image information of the white light and the special light from the first and second image information.

21. The observation image acquiring system according to claim 20,
    wherein the processor is configured to:
        select the first and second image information of the green region and the blue region as the same wavelength region; and
        generate the respective pieces of emphasized image information of the white light and the special light from the first and second image information.

22. An observation image acquiring method comprising:
    irradiating an observation target with first light in a wavelength region which does not include a wavelength region where an absorption peak of a target substance included in the observation target is present and second light in a wavelength region where the absorption peak is present;
    imaging the observation target irradiated with the first light or the second light to acquire image information; and
    performing an arithmetic operation for the image information acquired by the image sensor to generate emphasized image information which emphasizes the target substance,
    wherein generating the emphasized image information comprises:
        extracting absorption difference information indicating a difference of absorption of the target substance between first image information acquired when the observation target is irradiated with the first light and second image information acquired when the observation target is irradiated with the second light, wherein a period that the observation target is irradiated with the second light is different from a period that the observation target is irradiated with the first light; and
        adding the absorption difference information to the second image information to generate the emphasized image information.

23. The observation image acquiring method according to claim 22,
    wherein the generating the emphasized image information comprises:
        selecting the respective pieces of image information of the same wavelength region included in each of the first image information and the second image information; and
        extracting the absorption different information between the first color image information and the second color image information to generate the emphasized image information which emphasizes the target substance.

* * * * *